United States Patent [19]

Brown

[11] Patent Number: 4,652,830
[45] Date of Patent: Mar. 24, 1987

[54] ANALYZER FOR COMPARATIVE MEASUREMENTS OF BULK CONDUCTIVITY

[75] Inventor: Neil L. Brown, Sharon, Mass.
[73] Assignee: EG&G Ocean Products, Inc., Catamut, Mass.
[21] Appl. No.: 691,499
[22] Filed: Apr. 18, 1985
[51] Int. Cl.$^4$ ............................................. G01N 27/02
[52] U.S. Cl. .................... 324/439; 324/444; 324/99 D
[58] Field of Search .......... 324/439, 98, 99 D, 123 R, 324/442, 444; 346/31, 32; 330/171, 195; 307/350

[56] References Cited

U.S. PATENT DOCUMENTS 3,946,309 3/1976 Roughton et al. ............... 324/64
4,262,253 4/1981 Clark ........................... 324/442 X Primary Examiner—Reinhard J. Eisenzopf
Assistant Examiner—Robert W. Mueller
Attorney, Agent, or Firm—Wolf, Greenfield & Sacks

[57] ABSTRACT

Circuit for measuring the relative change in conductivity between two cells which include a test biorigion and a control biorigion as the test cell biorigion conductivity changes as a result of analyte modecules binding to receptor sites in the test cell biorigion. The invention includes circuitry for driving a current through each of the cells and for measuring the voltage drops across the test and control cells as a function of time. A novel two-stage ac analog-to-digital convertion circuit in which the initial conductivities are measured via a successive approximation process, while the relative conductivities are monitored during a test interval via a tracking technique is included. The circuitry is controlled by a digital controller which can vary the parameters of the measurement processes so as to make the circuit adaptable to the measurement of a wide variety of substances using different cell configurations and/or electrolytes.

1 Claim, 20 Drawing Figures

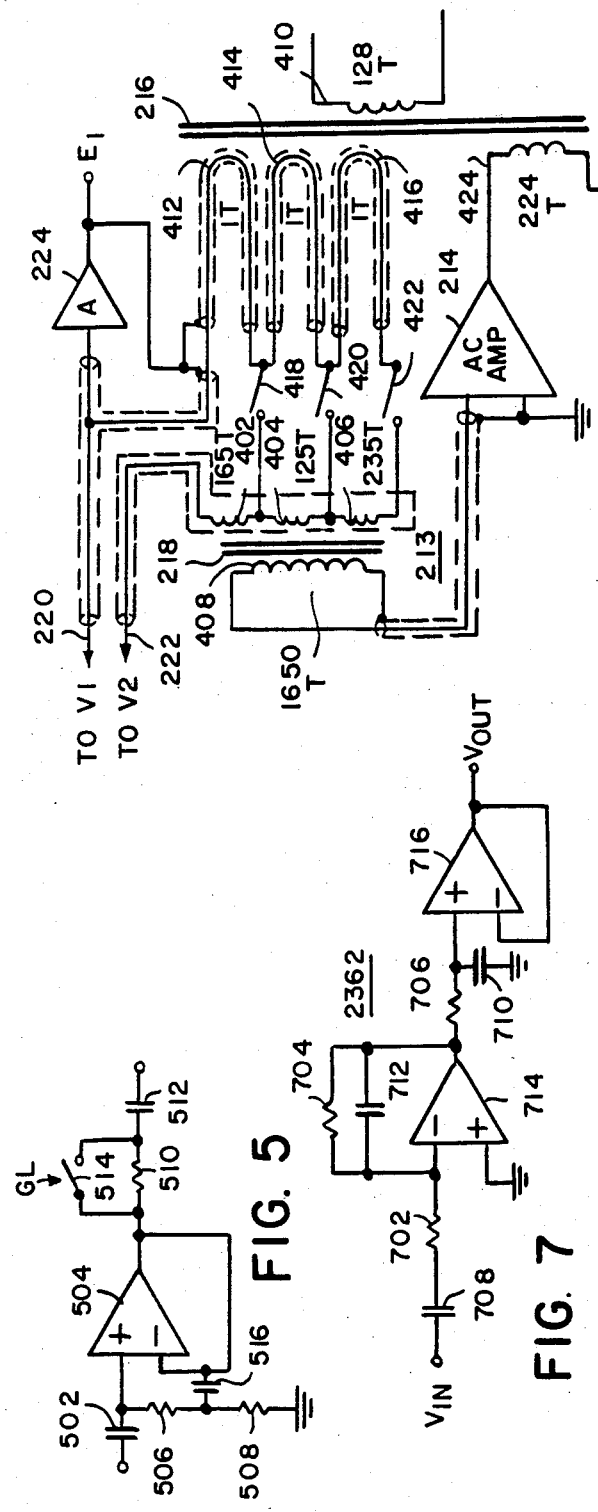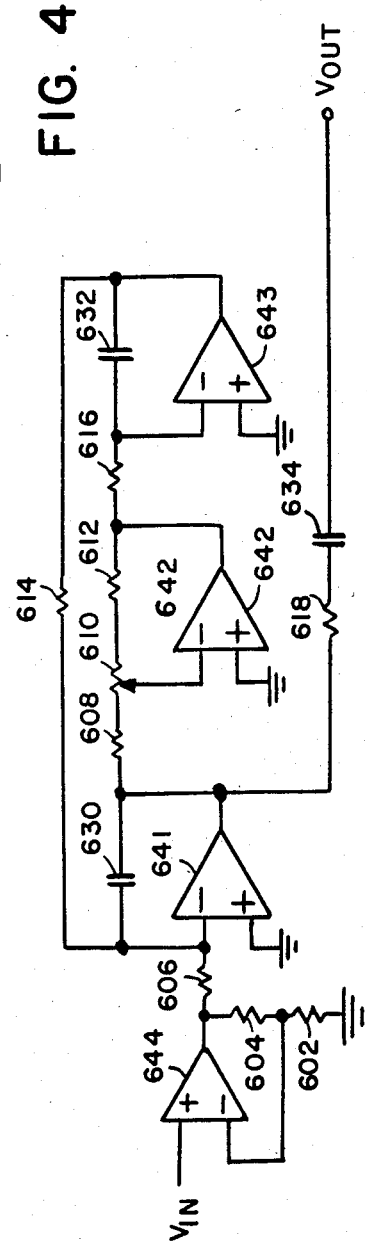

ANALYZER FOR COMPARATIVE MEASUREMENTS OF BULK CONDUCTIVITY

FIELD OF THE INVENTION

This invention is related to instruments for measuring bulk conductivity, and in particular for measuring the difference in conductivity between two individual cells as a function of time.

BACKGROUND OF THE INVENTION

There has recently been much work in the field of antibody-based assays to detect and measure the presence of particular substances. These types of assays often have several advantages over other methods of performing similar analysis, including high sensitivity in detecting small concentrations of a substance, high specificity for particular substances to be detected, and wide application to a large number of substances. Such tests rely on the ability of an antibody to bind to a particular antigen or other molecule. The bound antigen/antibody pair is then detected. Several methods exist for performing such detection of antigen/antibody complexes, for example, tagging the antigen or antibody with a flourescent or radioactive tracer which can be detected.

One method of detecting such an antigen/antibody complex involves the use of a matrix which contains an antigen or antibody which is immobilized in the matrix. In this method either the antibody or antigen may be the bound material in the matrix. More generally, such analyses can be performed using any type of ligand/antiligand pair, and the discussion of the operation of exemplary embodiments in terms of antibody/antigen pairs or other examples should not be considered to be a limitation on the applicability of the techniques of the present invention. The antigen or antibody which is bound will be referred to as the receptor and the antigen or antibody which is being detected will be called the analyte. The matrix including the bound receptors will be called the bioregion.

To detect or measure the presence of an analyte, it is typically diluted in a conductive solution such as a saline solution. The solution containing the analyte is then passed through the bioregion. The conductivity of the bioregion is measured by passing a current through the bioregion while measuring the voltage drop across the bioregion. As the analyte molecules are bound to the receptors in the bioregion, the cross-sectional area, and hence the volume, through which the current passes is reduced, and the conductivity of the biroregion decreases proportionately. Methods, sensing apparatus, and bioregions for performing these types of measurements are described in detail in a patent application Ser. No. 691,271 of D. Mitchell and R. Mitchell entitled "Measurement of Ligand/Antiligand Interactions Using Bulk Conductivity" filed Jan. 14, 1985 and incorporated by reference herein. This method of detecting and measuring an analyte in solution has many advantages of previously known methods for detecting substances, as described in the aforesaid application. Measuring the change in conductivity of such a bioregion presents novel problems which the present invention is directed towards solving.

SUMMARY OF THE INVENTION

The present invention includes circuitry for measuring the relative change in conductivity between two cells which include a test bioregion and a control bioregion as the test cell bioregion conductivity changes as a result of analyte molecules binding to receptor sites in the test cell bioregion. The invention includes circuitry for driving a current through each of the cells and for measuring the voltage drops across the test and control cells as a function of time. The invention is capable of measuring a change of $10^{-4}$ in the relative conductivity between the two cells with an accuracy of approximately one percent.

The invention includes a novel two-stage A.C. analog-to-digital conversion circuit in which the initial conductivities are measured via a successive approximation process, while the relative conductivities are monitored during a test interval via a tracking technique. The circuitry is controlled by a digital controller which can vary the parameters of the measurement processes so as to make the circuit adaptable to measurement of a wide variety of substances using different cell configurations and/or electrolytes. Extensive calibration and diagnostic capabilities are provided to ensure the accuracy of the measurements.

DESCRIPTION OF THE DRAWINGS

FIG. 4 is a schematic diagram showing further details of the transformer circuit of FIG. 2;

FIG. 5 is a schematic diagram showing further details of the shield and guard driver amplifiers of FIG. 2;

FIG. 6 is a schematic diagram showing further details of an AC bi-quad amplifier used in the circuit of FIG. 2;

FIG. 7 is a schematic diagram showing further details of the phase shifter circuit of FIG. 3;

DESCRIPTION OF THE PREFERRED EMBODIMENT

Figure 1B:
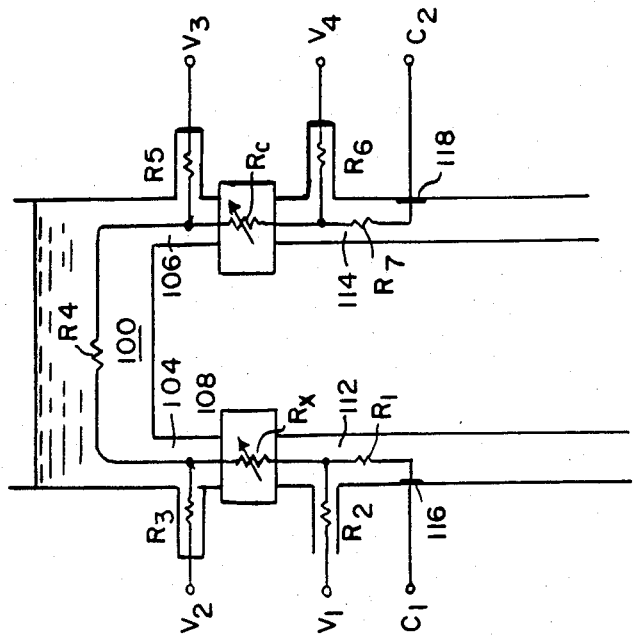
FIGS. 1A, 1B, and 1C are schematic illustrations of apparatus for passing a solution to be analyzed through test and control cell bioregions for measuring and comparing the relative conductivities of the cells.
Figure 1A:
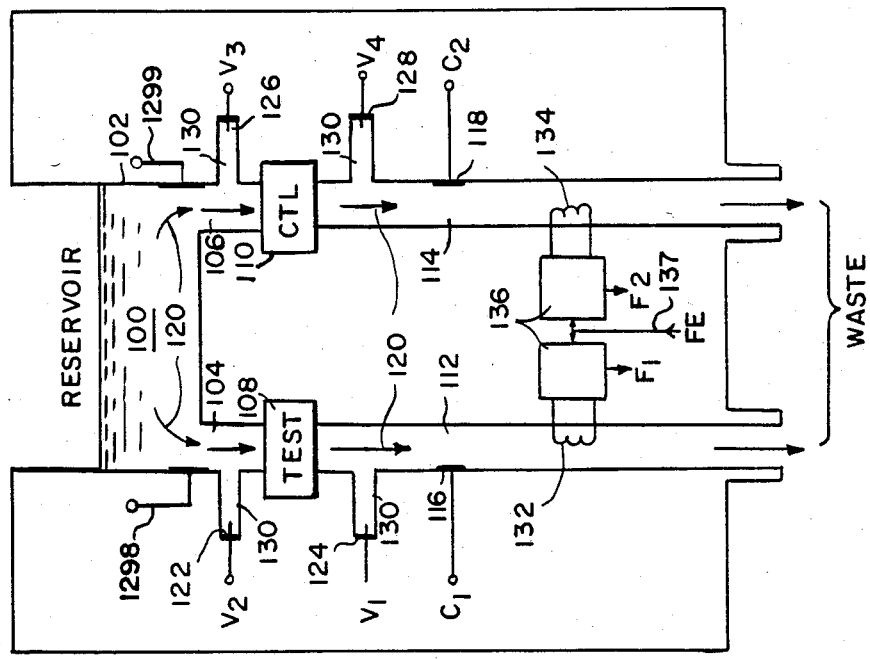
Figure 1C:
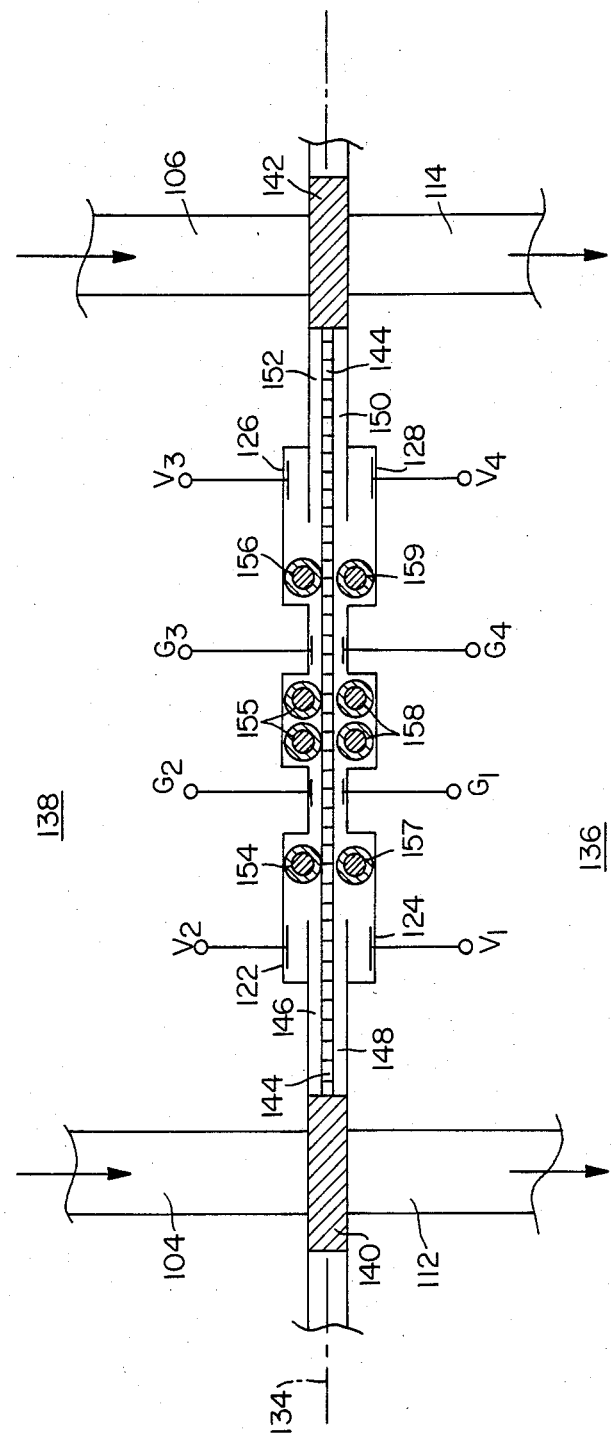

Referring to FIGS. 1A-1C, there is shown a diagramatic representation of a representative apparatus used in determining the presence or concentration of an analyte in a solution by measuring the change in the bulk conductivity of the bioregion as the analyte is bound to the receptors in the bioregion. FIG. 1A illustrates the physical arrangement of the cells, and FIG. 1B shows the electrical equivalent.

The embodiment described herein comprises a biolayer which includes two bioregions: a first bioregion, which will be referred to as the test cell or region, which includes receptors bound in a matrix so as to react with analyte molecules in the electrolyte, and a second bioregion, which will be referred to as the control cell or region, which includes a matrix similar to that in the test cell but without the receptor molecules. The characteristics of these cells are discussed in detail in the aforementioned patent application of D. Mitchell and R. Mitchell.

A reservoir 102 is filed with an electrolyte solution 100. Two channels 104 and 106 provide paths by which the electrolyte solution can flow from the reservoir, through the test regions, and eventually to a waste container. The fluid flow is illustrated by arrows 120 in FIG. 1A. The flow through channels 104 and 106 may be driven by gravity, pneumatic or hydraulic pressure, or other means. The electrolyte solution flows through paths 104 and 106 respectively into test region 108 and control region 110. The walls of the reservoir and fluid channels should be made of a non-conductive material.

The electrolyte from the test and control cells flows through two exit channels. A first current electrode 116 in channel 112 and a second current electrode 118 in channel 114 are respectively connected to terminals $C_1$ and $C_2$. A signal generator is connected to terminals $C_1$ and $C_2$ and causes a current to flow from current electrode 116 through channel 112, test cell 108, channel 104, reservoir 102, channel 106, control cell 110, and channel 114, to electrode 118. This current flow causes a voltage drop across the test and control cells which can be measured to determine the presence of a particular analyte in the electrolyte.

Two voltage electrodes 122 and 124 are connected to terminals $V_1$ and $V_2$ and contact the electrolyte solution on either side of the test cell 108. By measuring the voltage between the terminals $V_1$ and $V_2$, the conductivity of test cell 108 may be measured. Similarly, voltage electrodes 126 and 128 are connected to terminals $V_3$ and $V_4$ to provide a means for measuring the voltage drop across control cell 110.

Voltage electrodes 122 through 128 are typically recessed from the channels 104, 106, 112, and 114 through the electrolyte flows. Channels 130 in FIGS. 1A–1C represent this recession. Recession reduces errors which are caused by the effects of the electrode material on the current flow by removing the electrode from the electrolyte volume in which all or most of the current flows. The location of the current electrodes $C_1$ and $C_2$ well away from the voltage measurement regions, as shown in FIGS. 1A–1C, is equivalent to recessing these current electrodes. Other configurations for recessing the electrodes may also be used. Electrode polarization impedances can have significant capacitive parts which can contribute to quadratures errors in the measurement of the cell voltages. The magnitude of this quadrature error depends to a large extent on the geometry and other factors of the cell construction. Further discussion of reducing these effects of polarization impedances is contained in the above-described application by D. and R. Mitchell.

Flow measurement apparatus may optionally be provided downstream of the test and control cells to provide an indication of the volume of the flow of the electrolyte. In FIG. 1A, two hot wire flow sensors 132 and 134 are shown in the exit channels 112 and 114. In response to a flow measurement enable signal FE applied on line 137, circuitry 136 passes a current flow through the sensors and measures the heat conducted away from the sensors by the fluid flow to provide a measurement of the flow rate. Signals F1 and F2 represent the respective flow rates through test cell 108 and control cell 110.

FIG. 1B is an simplified electrical model representative of some of the the electrical characteristics of the arrangement of FIG. 1A. In FIG. 1B, $R_x$ is a resistance representing the conductivity of the bioregion in test cell 108. Similarly, $R_c$ represents the conductivity of control cell 110. Resistors $R_2$, $R_3$, $R_5$, and $R_6$ represent the resistance of the electrolyte solution in recession channels 130. Resistors $R_1$ and $R_7$ represent the resistance of the electrolyte solution between the current electrodes 116 and 118 and the test and control cells. Resistor $R_4$ represents the resistance of the electrolyte in the reservoir. It should be appreciated that the model shown in FIG. 1B is only a simplified model, but this model will be helpful in understanding the electronic circuitry described below which measures the conductivity changes in test and control cells 108 and 110.

The presence of a particular analyte in the electrolyte causes the conductivity of the test cell to change with time as the solution flows through the test and control cells. To briefly describe the process by which this is done, the bioregion within the test cell contains a matrix which includes receptors for detecting the presence of selected analytes. These receptors bind the analyte molecules within the test biolayer as the electrolyte flows through the test layer. As the amount of analyte bound within the test cell increases, there is a corresponding decrease in the volume and cross sectional area through which the test current flows resulting in a decrease in the conductivity of the test cell and an increase in the resistance between terminals $V_1$ and $V_2$.

Both the magnitude and the rate of change of the conductivity may be used to determine the presence of an analyte. Typically, a flow of pure electrolyte solution is established through the test cell until a steady state condition is reached, and the resistance is measured. Next, the material to be tested is added to the electrolyte in the reservoir, and the change in the resistance of the test cell is monitored.

Many other factors may affect the resistance between terminals $V_1$ and $V_2$, in addition to the change in the conductivity of the material in the test cell biolayer, however. For example, adding the material to be tested to the electrolyte may affect the conductivity of the electrolyte. Very small changes in temperature, flow rate, or other parameters of the electrolyte solution can also affect its resistance. The control cell is used to reduce or eliminate these errors from the measurement of the test cell conductivity.

Control cell 110 and it associated channels are constructed identically to test cell 108. The control cell includes a matrix material similar to the bioregion in the test cell except that the control cell does not contain any of the receptor material. Thus, the conductivity of control cell 110 is not changed by the presence of the analyte in the solution. By measuring the change in the conductivity of the test cell relative to the conductivity of the control cell, it is possible to reduce or eliminate variations in conductivity from effects other than analyte binding to receptor sites in the test cell.

A practical test instrument must be capable of performing successive test on various solutions quickly and inexpensively. In order to accomplish this, provision may be made to replace the bioregions in the test and control cells. A typical configuration to do this is illustrated (but not to scale) in FIG. 1C. The apparatus shown consists of a top section 138 and a bottom section 136 which may be separated along a plane designated by mid-line 134. A test cell bioregion 140 is connected to the control cell boregion 142 by an insulating material 144 to make a biolayer. This biolayer is placed between the top and bottom sections. Further details of this construction may be found in the above described application of D. and R. Mitchell.

The apparatus of FIG. 1C operates in the following manner. The test and control cell paths are symmetrical, as in FIG. 1A. For the test cell, fluid travels to the test cell in channel 104, through the bioregion 140, and exits through channel 112. Two fluid channels 146 and 148 above and below the insulating material 144 are filled with the electrolyte. These channels are equivalent to the recession channels 130 shown in FIG. 1A, and provide respective electrical paths between the top and the bottom of the biolayer 140 and electrodes 122 and 124 connected to terminals $V_1$ and $V_2$. The bioregions and the insulating layers in the test and control cells may extend further or less far than is shown in the diagram in FIG. 1C.

The control cell operates similarly with channels 150 and 152 providing electrical paths to the top and bottom of the control cell biolayer 142. O-rings 154 through 159 provide sealing to isolate the fluids in the test and control cells.

In operation, the structure of FIG. 1C is opened along mid-line 134 to allow the insertion of a new biolayer with fresh test and control cell bioregions. The top and bottom sections 136 and 138 are then reassembled with o-rings 154–159 providing sealing between the different fluid channels. Such a structure allows easy and inexpensive replacement of biolayers.

The sealing provided by the o-rings may not be perfect, however, and seepage of electrolyte past the o-rings may occur. Referring to FIG. 1C, if there is seepage past o-rings 154, 155, and 156, a resistive path between the test and control cells may result in errors in the measurements of the cell conductivities. To reduce or eliminate errors caused by such seepage, guard electrodes G1 through G4 are provided between each of the voltage measurement terminals $V_1$–$V_4$ and the adjoining seals. The operation of these guard rings is discussed in more detail below.

The parameter of importance to be determined in the apparatus of FIGS. 1A–1C is the ratio of the resistance, or conductance, of the test cell to that of the control cell, and more particularly the change in this ratio with time after the analyte is added to the electrolyte solution. As set forth in more detail in the reference application of D. Mitchell and R. Mitchell, this change may be very small, in some cases amounting to as little as one part in $10^{-4}$. The accuracy of the measurement should be one percent or better. Measurements may be taken over periods of time ranging from a few seconds to tens of minutes, and the resistance measurement circuitry must be extremely stable to provide the required accuracy over these time periods.

Figure 2:
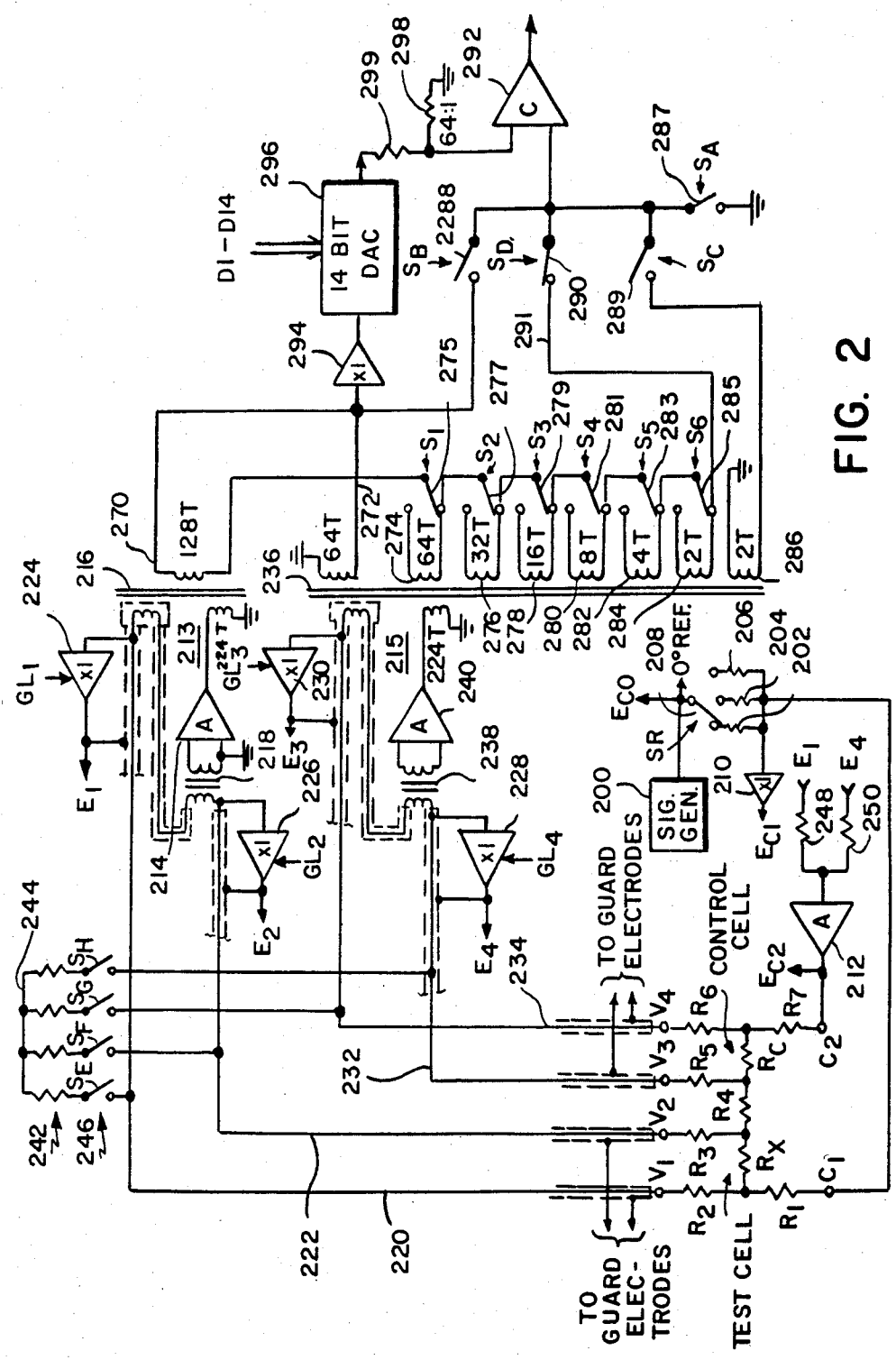
FIG. 2 is a block diagram of a circuit for measuring conductivity which embodies the present invention.

FIG. 2 is a schematic diagram of circuitry which can measure the relative change in conductivity between the test and control cells. As in FIGS. 1A and 1B, the test and control cells are represented by resistors $R_x$ and $R_c$; terminals $V_1$–$V_4$ are the voltage measurement terminals, terminals $C_1$ and $C_2$ are the current input terminals, and resistors R1–R7 represent the impedances of the fluid channels, which includes contributions of the fluid impedances, polarization impedances, and other effects.

In FIG. 2, a signal generator 200 provides a very pure sine wave output signal at a frequency of 384 Hz. While a higher frequency would make the design of the measurement circuitry more simple, problems with maintaining the accuracy of four-terminal measurements which result from capacitive effects, polarization impedances, and other error sources are lessened with the use of lower frequencies.

The signal generator output signal is applied to terminal $C_1$ through one of resistors 202, 204, or 206, as selected by a switch 208. In the described embodiment, resistors 202, 204, and 206 have values of 5K, 10K, and 15K ohms. Switch 208 and resistors 202–206 are used to match the output signal to the impedance of the test and control cells, depending on the electrolyte used and the cell configuration. Although switch 208 is shown as a manually-operated switch in FIG. 2, it could be controlled by the digital processor in alternate embodiments. The signal at terminal $C_1$ is also applied to a unity-gain buffer amplifier 210 which provides a buffered output signal $EC_1$ which is equal to the voltage at terminal $C_1$.

Terminal $C_2$ is driven by the output of an amplifier 212. As discussed in more detail below, amplifier 212 drives terminal $C_2$ so that the voltage at $C_2$ is equal in magnitude but opposite in phase to the voltage at terminal $C_1$ which causes a current to flow from terminal $C_1$ through the test and control cells to $C_2$, as described above in the description of FIGS. 1A and 1B. Noise pickup is minimized by providing a "balanced" drive to the current terminals $C_1$ and $C_2$.

The voltage between terminals $V_1$ and $V_2$ is applied to a high-input impedance, differential amplifier 213 comprised of amplifier 214 and transformers 216 and 218. This circuit is discussed in more detail below in connection with FIG. 4. The voltage across terminals $V_3$ and $V_4$ is applied to a similar amplifier circuit 215 including transformers 236 and 238 and amplifier 240. The operation of 215 is similar to that of amplifier circuit 213. In practice, the apparatus containing the test and control cells may be some distance away from the electronic measurement circuitry. The signals from terminals $V_1$–$V_4$ are applied to the differential amplifiers 213 and 215 through shielded cables 220, 222, 232, and 234.

Terminal $V_1$ is connected to the signal or center conductor of cable 220, and the signal at terminal $V_1$ is applied to one side of the primary winding of transformer 216. The signal on the center conductor of cable 220 is applied to the input of a unity-gain, high-impedance, buffer amplifier 224, which is physically located close to the electronic measurement circuitry. The output of amplifier 224 is connected to the shield of cable 224 and maintains the voltage on the shield at the same level as the signal on the signal conductor of cable 220. As shown in FIG. 2, the output of amplifier 224 also drives a shield around the primary winding of transformer 216 and a shield around the wire connecting the windings of transformers 216 and 218. The input to a second unity-gain buffer amplifier 226 is connected to the signal conductor of cable 226 near its connection to transformer 218. The output of amplifier 226 drives the shield of cable 222. Providing an active drive for the shield conductor reduces noise pickup and minimizes losses caused by capacitive leakage in cables 220 and 222.

The shield conductors of cables 220 and 222 may be connected to guard rings in the test cell to provide further reduction of errors. This may be better understood by referring to the diagram of the test and control cell configuration shown in FIG. 1C. As discussed above, fluid seepage around the o-ring seals may result in resistive leakage paths which will cause errors in the conductivity mesurements. The guard electrodes G1–G4 reduce or eliminate such errors. The guard electrodes are driven by the signals on the shields of the cables to each of the terminals. The resistance of electrical paths produced by leakage around the o-rings will be relatively high. Since the guard electrodes are maintained at a voltage equal to the voltage on the associated terminal $V_1$–$V_4$ by the low output impedance of amplifiers 224–230, any current flowing between the two cells will be principally provided by the guard electrodes. This reduces or eliminates errors which otherwise would be caused by electrical leakage along paths resulting from fluid seepage around the o-ring seals.

Signals $E_1$ and $E_2$ from the outputs of amplifiers 224 and 226 are buffered signals equal or approximately equal to the voltages at terminals $V_1$ and $V_2$. Signals $GL_1$ and $GL_2$ are applied to amplifiers 224 and 226 during diagnostic routines to enable the leakage current from the shield and guard electrode circuit for each amplifier to be measured, as discussed below.

The voltage across terminals $V_3$ and $V_4$ is processed by circuitry similar to the circuitry described above connected to terminals $V_1$ and $V_2$. The signals on terminals $V_3$ and $V_4$ are connected to the primary windings of transformers 236 and 238 by shielded cables 232 and 234. The signals on the center conductors of cables 232 and 234 are applied to amplifiers 228 and 230 which maintain the shields of the cables at a potential equal to the signal on the associated terminal and which provide buffered signals $E_3$ and $E_4$ equal to the voltages at terminals $V_3$ and $V_4$. Amplifiers 228, 230, and 240, transformer 238 and the primary winding of transformer 236 are essentially identical to the corresponding circuitry connected to terminals $V_1$ and $V_2$ except that terminals $V_3$ and $V_4$ are connected to this circuitry with the opposite polarity. In other words, the output signals from transformers 216 and 236 produced by a current flowing through the test and control cells will be opposite in phase from each other.

As described above, it is desirable to apply a voltage to terminal $C_2$ which causes the signals at $V_1$ and $V_4$ to be equal in magnitude but opposite in polarity. This is done by means of a negative feedback loop provided by amplifier 212. The $E_1$ signal is applied via a resistor 248 to the input of amplifier 212. The $E_4$ signal is similarly applied to the input of amplifier 212 via a resistor 250. Amplifier 212 is a relatively high-gain, inverting, Ac amplifier. In the described embodiment, amplifier 212 has a gain of approximately 10,000 at the operating frequency of 384 Hz. The $E_1$ and $E_4$ input signals applied to amplifier 212 are a function of the current driven through the test and control cells by amplifier 212, and the circuit forms a closed loop feedback circuit which forces the signal level at the input of amplifier 212 to zero or ground potential. In order for this to occur, the $E_4$ signal must be equal and opposite to the $E_1$ signal, which is the desired condition.

Each of the signal conductors of the cables may be selectively connected by switches 246 and resistors 242 to a common node 244. Although not shown in FIG. 2, the connection of switches 246 to the cables should be physically close to the inputs of the buffer amplifiers 224–230. In the described embodiment, resistors 242 each have a value of 1 kilohm. Switches 246 are electronically controlled switches. The four switches 246 are respectively controlled by signals $S_E$, $S_F$, $S_G$, and $S_H$ from the digital controller. Switches 246 may be selectively closed during diagnostic routines to provide a known resistance between the signal conductors of the cables. By comparing the voltages at terminals $V_1$–$V_4$ with switches 246 open and closed, leakage paths between the terminals may be determined, as discussed in more detail below.

The output winding 270 of transformer 216 has 128 turns and provides a signal proportional to the voltage drop across the test cell. Transformer 236 has multiple output windings, each of which provides a signal proportional to the voltage drop across the control cell. By selectively connecting the windings of transformer 236 in series the output of transformer 236 may be scaled with respect to the output of transformer 216.

Transformer 236 has a 64-turn output winding 272 one end of which is grounded. The second end of 64-turn winding 272 is connected to one end of output winding 270 of transformer 216. Transformer 236 additionally has six binary-weighted windings 274–284 having respectively 64, 32, 16, 8, 4, and 2 turns. Switches 275 through 285 are single-pole double-throw switches and are typically low-noise FET switches which are electronically controlled. In the present embodiment, six signals $S_1$–$S_6$ are applied to switches 274–285 by the digital processor to control the states of the switches. These switches are connected to windings 274–284 as shown in FIG. 2 so that any combination of the windings may be connected in series, depending on the settings of signals $S_1$–$S_6$. Thus, by appropriately setting the switches $S_1$–$S_6$, any even number of turns from 2 through 126 may be connected in series to provide an output signal which is proportional to the voltage drop across the control cell biolayer and which may be scaled over a range of of 1:126.

The signals from the various output windings of the two transformers 216 and 236 are summed in the following manner. One end of 64-turn winding 272 on transformer 236 is grounded. The second end of winding 272 is connected to one end of the single output winding 270 on transformer 216. The windings are connected so that the two windings are connected in series with the same phase. The second end of winding 270 is connected to the common terminal of switch $S_1$ so that the selected windings of binary-weighted windings 274–284 are connected in series with windings 270 and 272. The output from windings 274–284 is also in phase with the output from winding 270. Since, as described above, the input signals to transformers 216 and 236 are opposite in phase, the output signals from the two transformers are also opposite in phase.

The net effect of the above-described connection is that the signal from output winding 270 is connected in series, and thus subtracted (due to the oppositely-phased outputs) from the output signal from 64 to 190 turns of transformer 236, depending on the settings of switches $S_1$–$S_6$. In other words, by properly setting switches $S_1$–$S_6$, the output signal from transformer 236 may be scaled so that it is approximately equal to the output signal from transformer 216 for voltage drops across the test cell ranging from about 50% to 150% of the voltage drop across the control cell. The signal on line 290 represents the contact difference of the output signals from transformers 216 and 236.

The output from the 64-turn winding 272 is applied via a unity-gain buffer amplifier 294 to the analog input of a 14-bit, multiplying digital-to-analog converter (DAC) 296. DAC 296 may be implemented, for example, by an ICL 7134 integrated circuit. Fourteen digital input signals $D_1$–$D_{14}$ are applied to the DAC by the digital processor. In response to signals from the digital processor, the output from winding 272, which is proportional to the voltage drop across the control cell, may be scaled over a range of $2^{14}$. The output from DAC 296 is applied to a resistive 64-to-1 divider made of resistors 298 and 299. This divider scales the output of the DAC so that one MSB of the DAC is equivalent to the output from one turn to the windings on transformer 236. In this manner, the selectable output windings of transformer 236 and the DAC 296 allow the output from the control cell to be scaled over a 20-bit range.

The output from resistive divider 298-299 is applied to one input of a comparator 292. The second input to the comparator is selected by switches 287-290. These switches are respectively controlled by signals $S_A$-$S_D$ from the digital processor. Closing switch $S_A$ connects the second input to comparator 292 to ground; switch $S_B$ connects the input to the output of 64-turn winding 272; $S_C$ to the output of 2-turn winding 286; and switch $S_D$ to the output of series-connected windings 270, 272, and 274-284, as determined by the setting of switches $S_1$-$S_6$. Switches $S_A$-$S_C$ are used during calibration, and the operation of these switches is discussed in detail in connection with FIGS. 8-10.

During conductivity measurements, switch $S_D$ is closed to connect the second input to the comparator to the series-connected windings 270, 272, and 274-284. In this mode, the test cell output signal from 128-turn winding 270 is effectively subtracted from the control cell signal as scaled over a range of approximately 0.5 to 1.5, depending on the signals $S_1$-$S_6$ applied to the selectable windings 274-284. The $S_1$-$S_6$ signals are set by the digital processor so that the control cell output from the windings of transformer 236 approximates as closely as possible the test cell output signal from transformer 216. The first input to the comparator is provided by the DAC 296 scaled by 64:1 divider 298-299. The maximum output from the divider is equal to one-half of the smallest increment provided by the settings of switches $S_1$-$S_6$.

Thus, the combination of the six MSB's provided by the transformer winding switches $S_1$-$S_6$ and the 14 LSB's provided by the DAC provides a 20-bit conversion of the test cell signal effectively using the control cell signal as a reference voltage for the conversion. The described circuit takes advantage of the high accuracy of a precision-ratio transformer in determining the most significant bits, which do not change often, while allowing fast tracking of the changing test cell signal by using the multiplying DAC 296 to provide the least significant bits.

Figure 3:
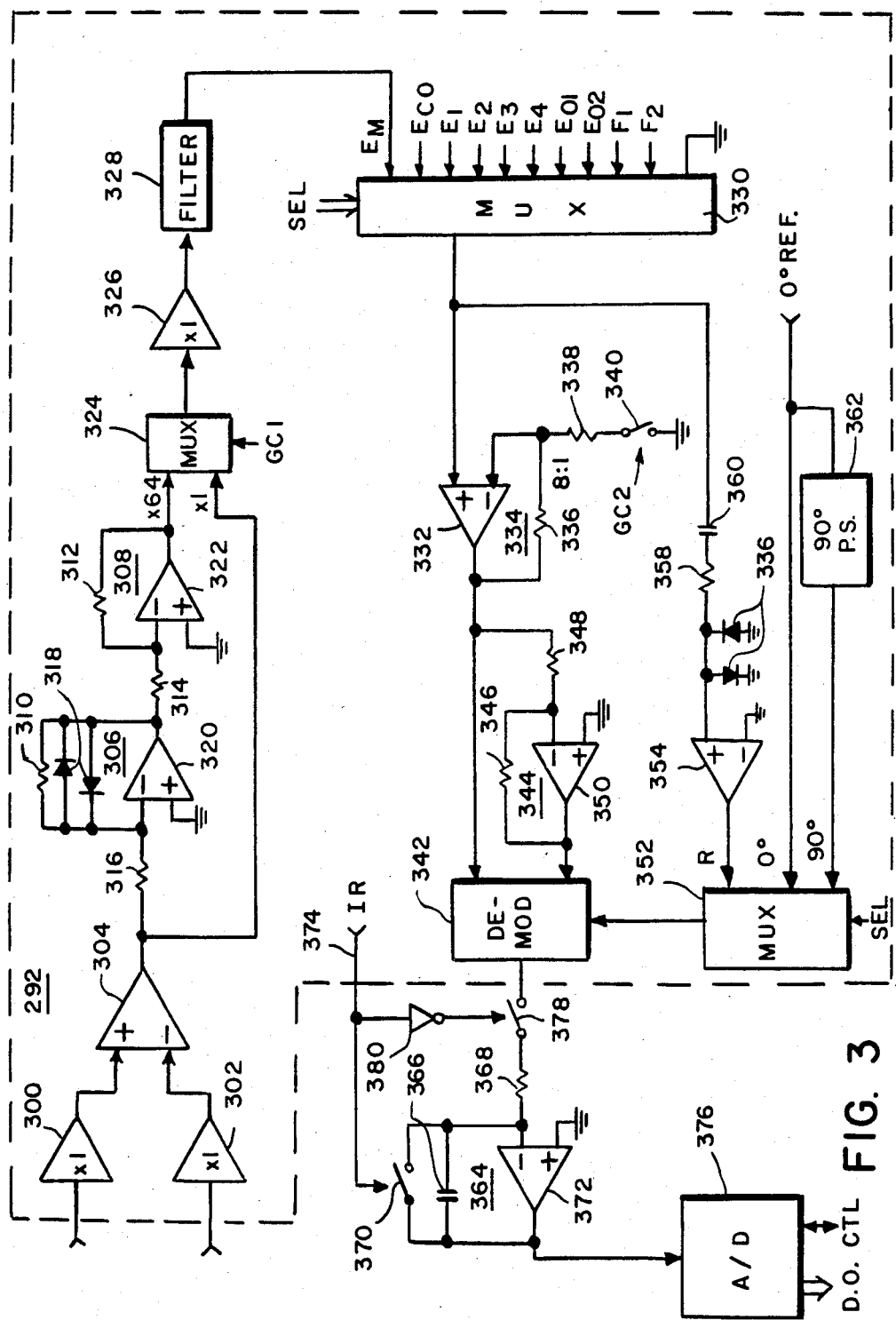
FIG. 3 is a schematic diagram showing further details of the comparator circuit of FIG. 2.

FIG. 3 shows the comparator circuitry in more detail. The two inputs to comparator 292 are applied to two, unity-gain, buffer amplifiers 300 and 302 whose outputs are applied to a precision differential amplifier 304. The output of amplifier 304 is directly applied to one input of a multiplexer 324. The output of amplifier 304 is also applied to multiplexer 324 via two amplifier stages 306 and 308, each of which have a gain of 8 for a total gain of 64. A gain control signal $GC_1$ is applied to multiplexer 324 by the digital processor to select a gain of 1 or 64 for the output signal from amplifier 304.

Amplifier stages 306 and 308 are made up of op-amps 320 and 322 connected as inverting amplifiers as shown in FIG. 3. Resistors 310-316 are chosen to give a gain of 8 for each amplifier stage. Opposed diodes 318 are connected in parallel across the feedback resistor to the first amplifier stage 306 to limit the output signal amplitude. Although a gain value should be selected to keep the operation of amplifier stages 306-308 and the following circuitry in the linear region, noise spike may be present. If such spikes were to drive any of the circuitry of comparator 292 into saturation, large errors might result. Diodes 318 serve to suppress any such noise spikes.

The output of multiplexer 324 is applied via buffer amplifier 326 to an AC bandpass filter circuit. It is important that filter circuit 328 has a high attenuation of frequencies removed from the signal frequency of 384 Hz while maintaining a very flat phase characteristic. One circuit suitable for implementing filter 328 is the bi-quad amplifier circuit described in my U.S. Pat. No. 4,539,525, "Bandpass Amplifier Filters." Other circuits known to those in the art may also be used to implement filter 328.

The output of filter 328 is applied to one input of a multiplexer 330. Other signals applied to multiplexer 330 include the $E_1$-$E_4$ signals, representative of the voltages at terminals $V_1$-$V_4$, the $EC_1$ and $EC_2$ signals, representative of the voltages at the current terminals $C_1$ and $C_2$, the F1 and F2 signals, representative of the flow in each of the test and control cells, and ground. Multiplexer 330 normally connects the output of filter 328 to the input of amplifier stage 334 when the circuit is measuring the conductance of the test or control cells. The digital processor provides the appropriate SEL input to multiplexer 330 to measure the other signals applied to the multiplexer for calibration and diagnostic purposes, as discussed below. It should be noted that the signals applied to multiplexer 330 are AC signals which must be demodulated prior to being measured.

The output of multiplexer 330 is applied to the non-inverting input of an op-amp 332 of amplifier stage 334. A feedback resistor 336 is connected between the output and inverting input of the op-amp. A second resistor 338 is connected to the inverting input of the op-amp and is also selectively connected to ground through a switch 340. The ratio of resistors 336 and 338 is 8 to 1. By closing switch 340, a gain of 1 or of 8 may be selected for amplifier stage 334. Switch 340 is typically a low-noise FET switch which is controlled by a signal $GC_2$ provided by the digital processor.

The output from amplifier 334 is applied to one input of a demodulator circuit 342 directly, and to a second input of the demodulator via a unity-gain inverting amplifier stage 344, made up of op-amp 350 and resistors 348 and 348. Demodulator 342 may be implemented, for example, by AD 534L balanced multiplier circuit. Inverting amplifier 344 provides a signal equal to the signal from amplifier 332 but 180 degrees out of phase. This signal is applied to the second input to the balanced demodulator. It is desirable to use a balanced type of demodulator to provide as stable a signal as possible at the demodulator output. The output signal from the demodulator represents the value of the difference between the test and control cell voltages.

The reference input signal to demodulator 342 is selected by a multiplexer 352. The signal from multiplexer 352 is a reference clock signal derived from signal generator 200 which is used to demodulate the AC signal applied to the balanced inputs to the demodulator. A 0-degree reference signal taken directly from the signal generator is applied to one input of the multiplexer. This signal is normally used to demodulate the input to the demodulator, as discussed below, when the conductivity of the control and test cells is measured.

Although, in theory, the signals applied to the comparator circuitry 292 should be exactly in phase with the output signal from signal generator 200, small phase shift errors may be introduced by parasitic impedances in the circuitry and other error sources. These phase errors can cause errors in the amplitude of the demodulated signal, since the reference signal will no longer be exactly in phase with the signal to be demodulated. Two other reference signals may be selected by multiplexer 352 which allows such errors to be measured so that proper compensation can be made.

A second signal is applied to the multiplexer by limiting amplifier 354. This signal is designated as the random reference signal, since its phase relationship to the clock signal is not exactly known. The output from multiplexer 330, which is the signal to be demodulated, is applied via capacitor 360 and resistor 358 to one input of an op-amp 354. Two opposed diodes 356 are connected between the input of the op-amp and ground to limit the input voltage to the op-amp. The op-amp is operated in open loop mode and provides at its output a square wave signal in phase with the output from multiplexer 330. By demodulating the output from multiplexer 330 with this signal, the magnitude can be determined independent of any unknown phase shifts which the prior circuitry may have introduced.

A third signal is applied to multiplexer 352 from a 90-degree phase shifter circuit 362. The 0-degree reference is applied to the input of 90-degree phase shifting circuit 362. Phase shifter 362 provides a precise 90 degree phase shift to the 384 Hz input signal and provides a reference clock signal in phase quadrature to the 0-degree signal. During diagnostics, the input to the demodulator may be demodulated using the random and 90-degree reference signals as well as the 0-degree reference to determine exactly the quadrature component introduced into the signal to be measured from the test and control cells. The digital processor may use this information to ensure that the quadrature error is not so large as to result in erroneous measurements and optionally to correct the measured conductivity value, if such corrections are needed.

The output from the demodulator is applied to a precision reset-integrator circuit 364. Integrator 364 is implemented using a high gain precision amplifier 372, input resistor 368, and integrating capacitor 366. Capacitor 366 should be a polypropylene or other similar type capacitor having high stability. Typical values for resistor 368 and capacitor 366 are 100 kilohms and 1.0 microfarads. An electronic switch 370 is connected across the capacitor and is controlled by an integrator reset signal IR.

A second switch 378 is connected in series with the input to the integrator and is controlled by an inverted IR signal from an inverter 380. Thus, when the IR Signal is inactive, switch 370 is closed to reset the integrator while switch 378 disconnects the input signal to the integrator. When the IR signal goes active, the input signal is applied to the integrator and the reset switch 370 is opened, allowing the integrator 364 to integrate and filter the output signal from the demodulator.

The output signal from the demodulator is applied to the input of an A/D converter 376. Converter 376 may be implemented, for example, by means of an AD5-74AJD 12-bit bipolar A/D converter circuit manufactured by Burr Brown. This converter performs a conversion in approximately 25 microseconds, which is essentially instantaneously with respect to the rate of change of the output from integrator 364. A/D converter 376 is controlled by signals to and from the digital processor, represented by the CTL signals to and from converter 376 in FIG. 3. The digital output values are read by the digital processor after each conversion is performed.

As will become more clear after reading the discussion of the measurement procedures explained below in conjunction with FIGS. 8–11, the present invention allows a very low noise measurement to be made of the test and control cell conductivities using a method which requires essentially no settling time during the period that the circuitry is tracking the change in conductivity of the test cell. Further, the finite time integration provided by integrator circuit 364 provides near optimal filtering of noise which may be present in the signals from the cells.

FIG. 4 shows further details of input amplifier circuitry 213 connected to terminals $V_1$ and $V_2$. The operation of the amplifier circuitry 215 connected to terminals $V_3$ and $V_4$ is similar, except that transformer 236 has multiple secondary windings while transformer 216 has a single secondary winding, as discussed above. In order to maintain accuracy, it is important the the output signals from transformer 216 have a precise relationship to the signals from transformer 236. By using precision-ratio transformers for transformers 216 and 236, the output voltages from the various windings can be made accurate to better than one part in $10^6$.

In FIG. 4, transformer 218 has an input winding with two taps to provide three winding segments 402, 404, and 406 having 165, 125, and 235 turns respectively, and a single 1650-turn output winding 408. Transformer 216 is a precision ratio transformer and has a 224-turn input winding 424, a 128-turn output winding 410, discussed above in connection with FIG. 2, and three single-turn output windings 412, 414, and 416. One end of winding 416 is connected to the lower tap of transformer 218 via a switch 422. Similarly the two taps to the connections between windings 412 and 414 are selectively connected to the two taps on winding 218 via switches 418 and 420. One of switches 418–422 is closed during operation to select the gain of the amplifier stage. The impedance across the windings of transformer 218 is much larger than the impedance across the single turn windings 412–416, and transformer 218 ensures that a high enough impedance is provided to the sensors. Transformer 218 also serves to isolate the four electrodes from the analog ground.

The secondary winding of transformer 218 is connected to the input of an AC amplifier 214. Amplifier 214 has a very high gain at the operation frequency of 384 Hz, typically on the order of 100,000, while maintaining a very stable phase shift. The output of Amplifier 214 is connected to input winding 424 having 224 turns on transformer 216. The input of amplifier 224 is connected to the line going to terminal $V_1$. Its output is connected to the shields of the cables providing the input to transformer 218. These shields include the shield of line 220 and the shields of each of the single-turn windings 412–416. The shield of line 222 to terminal $V_2$ is similarly driven by amplifier 226, not shown in FIG. 4. The input windings 402–406 of transformer 218 are shielded, and this shield is also connected to and driven by amplifier 226.

Amplifier 213 serves to provide a high impedance across terminals $V_1$ and $V_2$ and also provides a relatively high impedance to the input of amplifier 214. The gain of amplifier 213 is determined by the ratio of single-turn windings 412-416 to output windings 410 and is thus very accurate and stable. This is done in the following manner.

The connection from the output of amplifier 214 through transformers 216 and 218 back to the input of amplifier 214 provides negative feedback. Due to the high gain of amplifier 216, the negative feedback makes the input to amplifier 214 a virtual ground. The voltage across the output winding of transformer 218 must therefore be essentially zero, and hence the voltage across the selected input winding of transformer 218 must also be zero. Since the voltage drop across the input winding 402-406 to transformer 218 and the single-turn windings 412-414 must equal the voltage across terminals $V_1$ and $V_2$, essentially the entire voltage across $V_1$ and $V_2$ appears across the single turn windings 412-416. The gain from lines 220 and 222 (connected to the inputs to amplifier 213) to the output winding 410 is essentially determined solely by the ratio between the number of windgs selected by switches 418-422 and the 128-turn output winding 410. By selectively closing switches 418-422, gains of 128, 128/2, and 128/3 may be selected. Switches 418-422 and the different taps on transformers 216 and 218 enable a relatively constant input impedance to amplifier 214 to be maintained when the amplifier gain is changed.

FIG. 5 shows one circuit suitable for amplifiers 224, 226, 228, and 230 which drive the shields of the cables to terminals $V_1$-$V_4$ and the guard electrodes. The input signal is applied to the non-inverting input of an op-amp 504 through a capacitor 502. Op-amp 504 may be implemented by LF356 amplifiers. The output of op-amp 504 is connected to its inverting input to provide a unity-gain amplifier. Two large value resistors 506 and 508 are connected in series between the non-inverting input to the op-amp and ground to provide a DC reference level at the input. A capacitor 508 connects the junction of resistors 506 and 508 and the op-amp output.

The output from the op-amp is connected through a capacitor 512 and a resistor 510 in parallel with switch 514 to provide the amplifier stage output signal. Resistor 510 is typically 1 kilohm. Switch 514 is an electronically controlled switch such as a FET switch and is normally closed during conductivity measurements. During diagnostic routines, the processor provides a guard leakage measurement signal GL which opens switch 514, putting resistor 510 in series with the output signal to the shields and guard electrodes. If there is no leakage current flowing from the guard and shield circuit, the $E_1$ through $E_4$ voltages will remain the same when switch 514 is closed. If there is any signficant leakage current, the leakage current will cause a voltage drop across resistor 410. By measuring the $E_1$ through $E_4$ voltages with switches 514 closed and open, the leakage current in each shield and guard electrode circuit can be determined.

FIG. 6 is a schematic of an AC amplifier circuit which may be used for the AC amplifier 212. The circuit consists of four 5532 op-amps 641-644 connected as a bi-quad amplifier/filter, as shown in FIG. 6. This amplifier configuration is discussed more fully in U.S. Pat. No. 4,539,525, "Bandpass Amplifier Filters," and is assigned to the assignee of this application. The circuit provides an open-loop gain of approximately 30,000 while maintaining a very stable zero-phase shift characteristic around the operating frequency of 484 Hz. Typical values for the components shown in FIG. 6 are as follows:

602: 100 ohms
604: 10K
606: 150K
608: 10K
610: 1K
612: 10K
614: 51K
616: 49.9K
618: 4.99K
630: 0.0082 mfd.
632: 0.002 mfd.
634: 2.2 mfd.
641: 5532
642: 5532
643: 5532
644: 5532

The circuitry of AC amplifiers 214 and 240 may be implemented by means of a two stage bi-quad amplifier circuit. One such circuit suitable for use with the described embodiment and which includes compensation for DC offset errors is shown in the above-referenced patent application for "Bandpass Amplifier Filters" in FIGS. 8 and 9 thereof.

FIG. 7 is a schematic diagram of one circuit for implementing the 90-degree phase shifter 362. The input signal to the phase shifter circuit is applied through series-connected capacitor 708 and resistor 702 to the inverting input of an op amp 714. The inverting input of the op-amp is grounded. A resistor 704 and capacitor 712 are connected in parrallel between the output and the inverting input to op-amp 714. An op-amp 716 is connected as a unity-gain buffer amplifier. The output of op-amp 714 is applied to the input of the second op-amp 716 via a resistor 706. A capacitor 710 is connected between the input to op-amp 716 and ground. Typical values for the components in FIG. 7 are as follows.

702: 40K
704: 4 megohms
706: 8.2K
708: 1.0 mfd.
710: 0.001 mfd.
712: 0.01 mfd.
714: LF356
716: LF356

FIGS. 8A through 10C are flow diagrams showing the steps and methods performed by the digital processor controller to carry out a conductivity measurement. It is assumed that to start, the instrument cells and reservoir are filled with electrolyte, that the solution is flowing through the system, and that the material to be analyzed has not yet been added to the electrolyte.

Figure 8A:
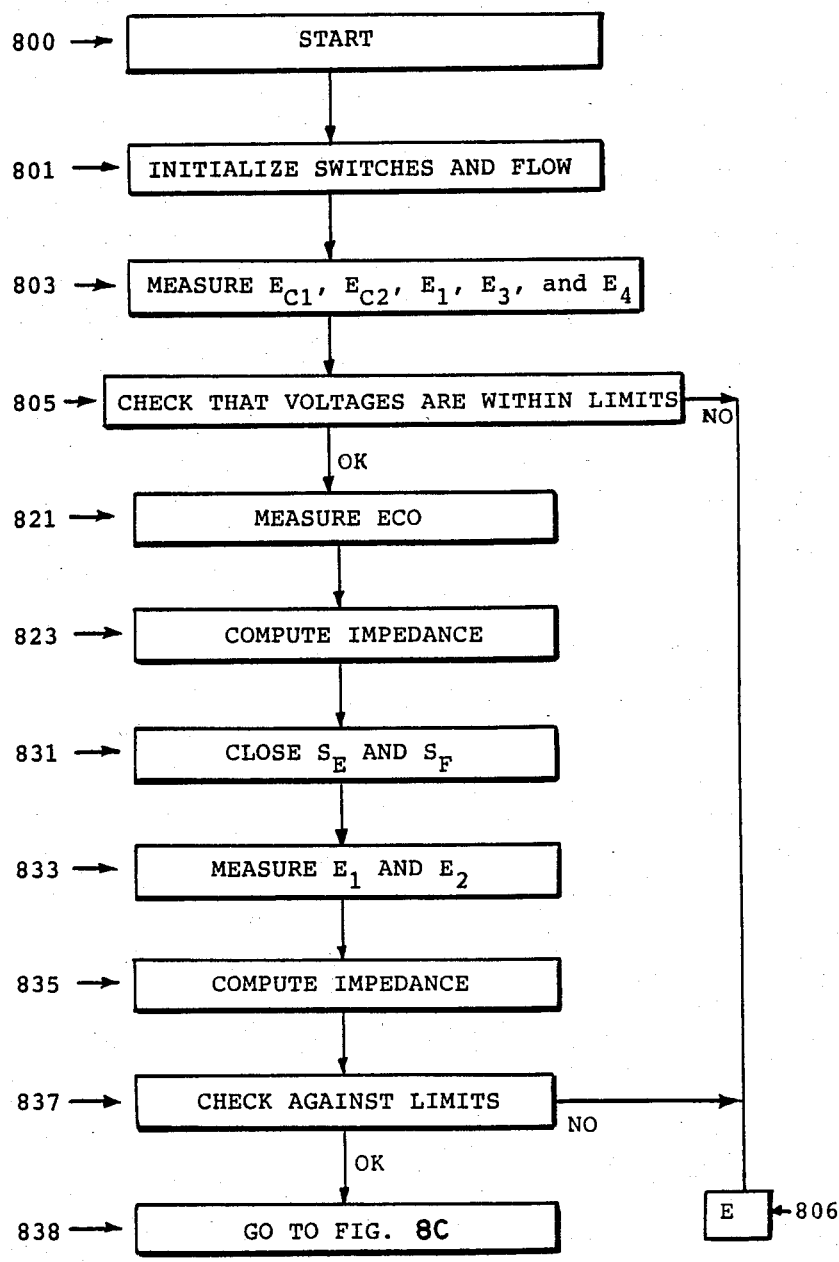
FIGS. 8A-8E, 9A-9B, and 10A-10C are flow diagrams showing one method by which a measurement of conductivity may be performed by the circuitry described herein.

FIG. 8A shows the initial diagnostic routines performed by the instrument prior to making conductivity measurements. First, the processor initializes the machine including setting all switches and, if the flow is under control of the processor, block 801. Switches $S_E$-$S_H$ are all put into their open position. Switch $GC_2$ is set to the high gain position, and the random reference signal is selected by multiplexer 352 for the initial measurements during which the magnitude of various signals is measured.

Next, the instrument measures the values of $EC_1$ and $EC_2$, and $E_1$ through $E_4$. The digital process does this by sending signals to multiplexer 330 which sequentially applies each of these signals to the input of amplifier 332 and then measuring the voltage, block 803. For each signal, the processor checks to ensure that each of these voltages are within predetermined limits, block 805. If not, the processor goes to an error routine, denoted by branch point E, where an appropriate error message is output to the operator and the measurement process is aborted.

Figure 8B:
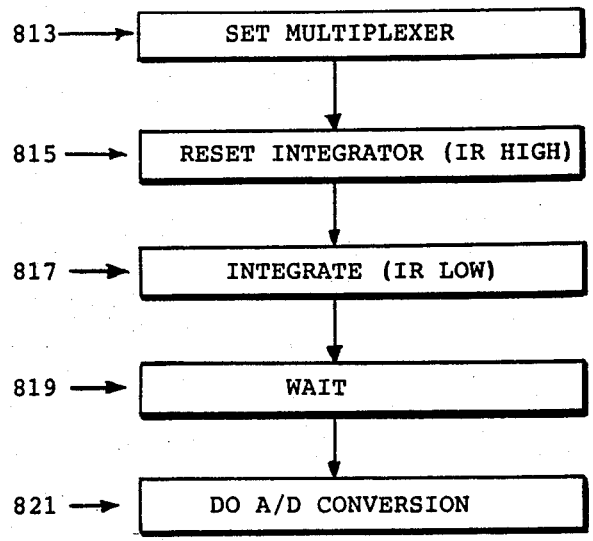
Figure 8E:
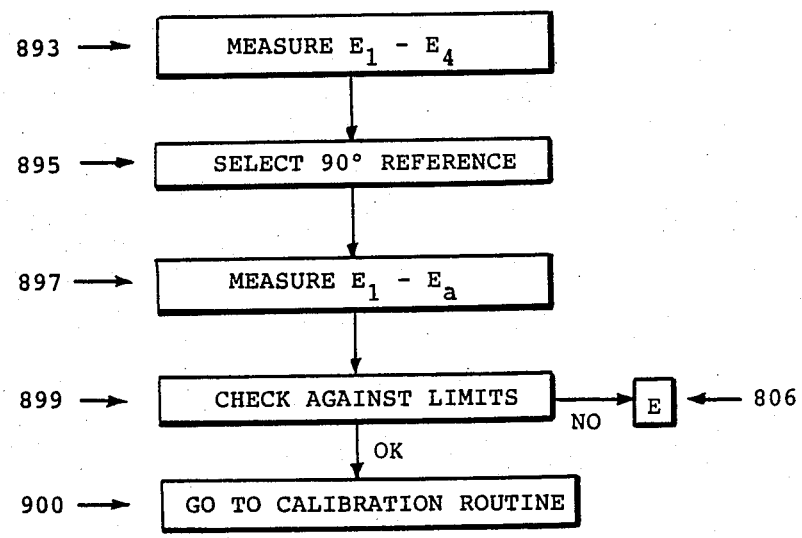
Figure 8C:
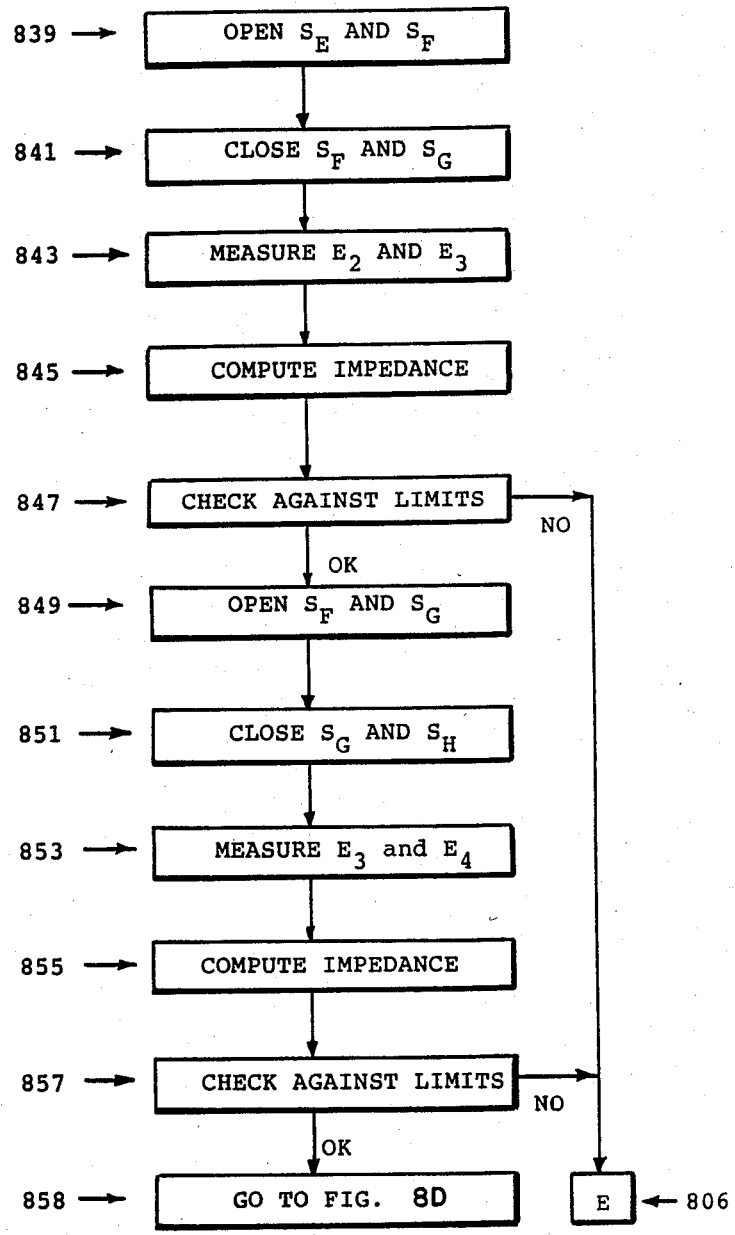
Figure 8D:
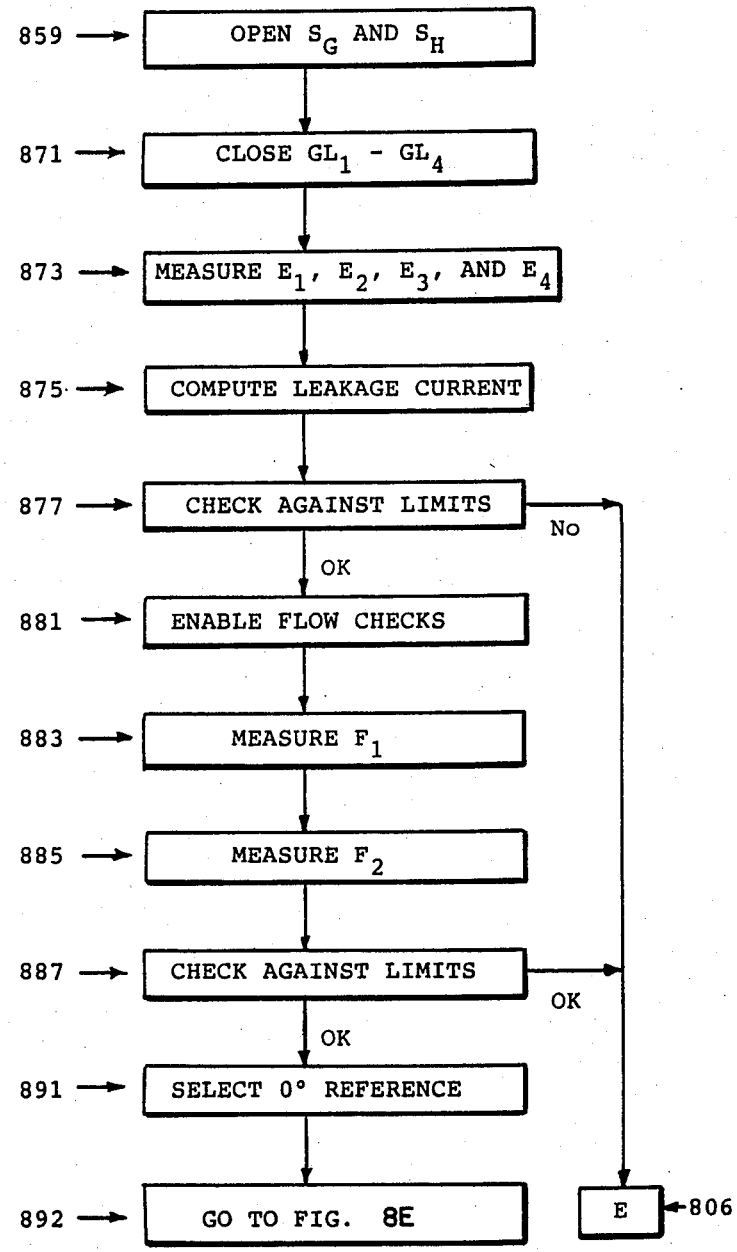

FIG. 8B is a brief flow diagram of how voltage measurements are made during the diagnostic routine, such as those performed in block 803. First, multiplexer 330 is commanded to select the proper signal, block 813. Next, the IR signal is set high to reset the integrator, block 815. The processor waits for at least 1 millisecond to allow the integrator capacitor to completely discharge. The IR signal is then set low to start the integration of the demodulated signal, block 817. The processor waits for a predetermined time, block 819, and then commands the A/D converter to convert and measure the output voltage from the integrator, block 821.

Returning to FIG. 8A, if the voltages measured during block 805 are within the proper limits, the processor proceeds to determine the current flowing through the cells. This is done by measuring the $EC_0$ voltage at the output of signal generator 200, block 821. The processor then computes the value of the cell current from the values of $EC_1$, $EC_0$, and the signal generator resistance selected by $S_R$, block 823.

The processor next checks the impedances between terminals $V_1$ and $V_2$. This is begun by closing switches $S_E$ and $S_F$, block 831, which connects of the two 1-kilohm resistors 242 between terminals $V_1$ and $V_2$. Next $E_1$ and $E_2$ are measured, block 833. From the previously computed value of the current and the values of $E_1$ and $E_2$ with and without the resistors 242 connected, the impedance between terminals $V_1$ and $V_2$ is computed, block 835. This value is then checked against its limit values, block 837.

If the impedance is within the limits, switches $S_E$ and $S_F$ are opened, block 839, and the above procedure is repeated to measure the impedance between terminals $V_2$ and $V_3$, blocks 841-849, and between $V_3$ and $V_4$, blocks 851-859.

Next the guard electrode leakage currents are checked, blocks 871-877. First, switches $GL_1$ through $GL_4$ are closed, block 871, and the voltages $E_1$ through $E_4$ are measured with the resistors 510 shown in FIG. 5 in series with the guard electrode. From the change in each of the voltages $E_1$ through $E_4$ with and without resistors 510 in series with the guard electrodes, the leakage current for each of the four lines is computed, block 875, and compared against the limit values, block 877.

If the flow rate is checked, this is done next, blocks 881-887. If necessary, the flow measurement apparatus is enabled by the FE signal, block 881. The flow signals F1 and F2 are then measured, blocks 883-885, and checked against their limit values, block 887.

To end the diagnostic routine, a check is made to ensure that the signals from the cells are properly phased, blocks 891-899. This check ensures that a short or other malfunction has not shifted the phase of one of the signals from terminals $V_1-V_4$. The previous measurements of $E_1-E_4$ were made with the random reference selected by multiplexer 352 for the demodulation. First, the processor commands multiplexer 352 to select the 0-degree reference signal, block 891. The values of $E_1-E_4$ are then measured, block 893. The multiplexer is then commanded to select the 90-degree reference, block 895. The values of $E_1-E_4$ are measured again, block 897. Finally, the measured values are checked to ensure that signals from terminals $V_1-V_4$ are within allowable limits, block 899. If so, the processor proceeds to the calibration routines, block 900.

Figure 9A:
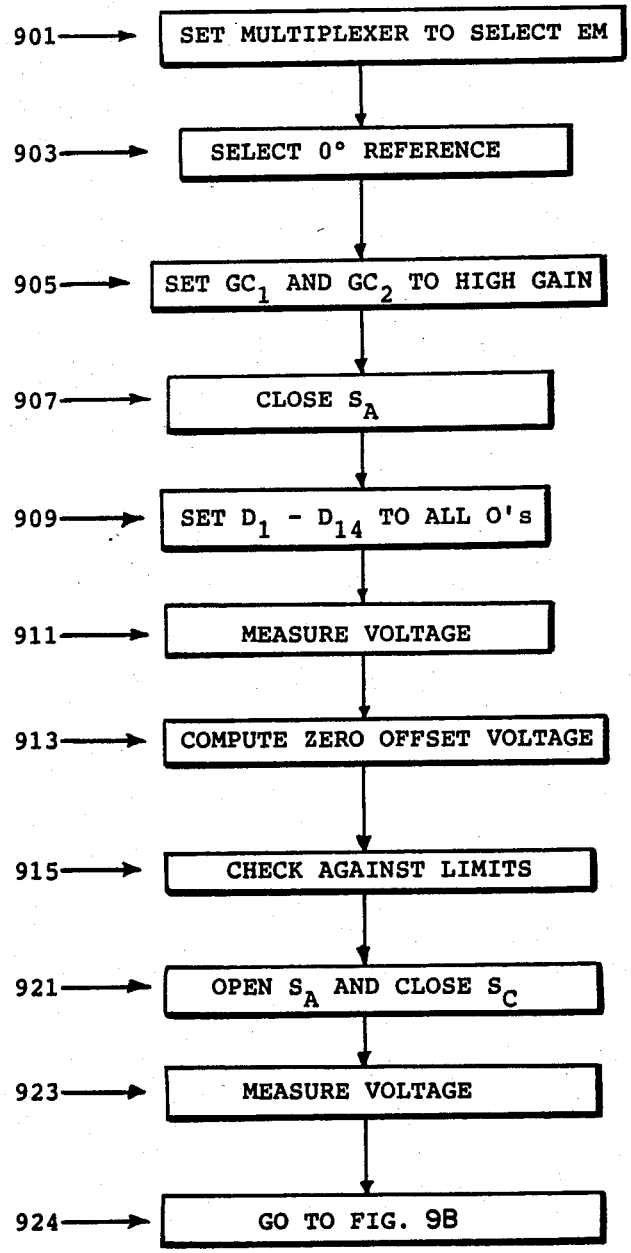
Figure 9B:
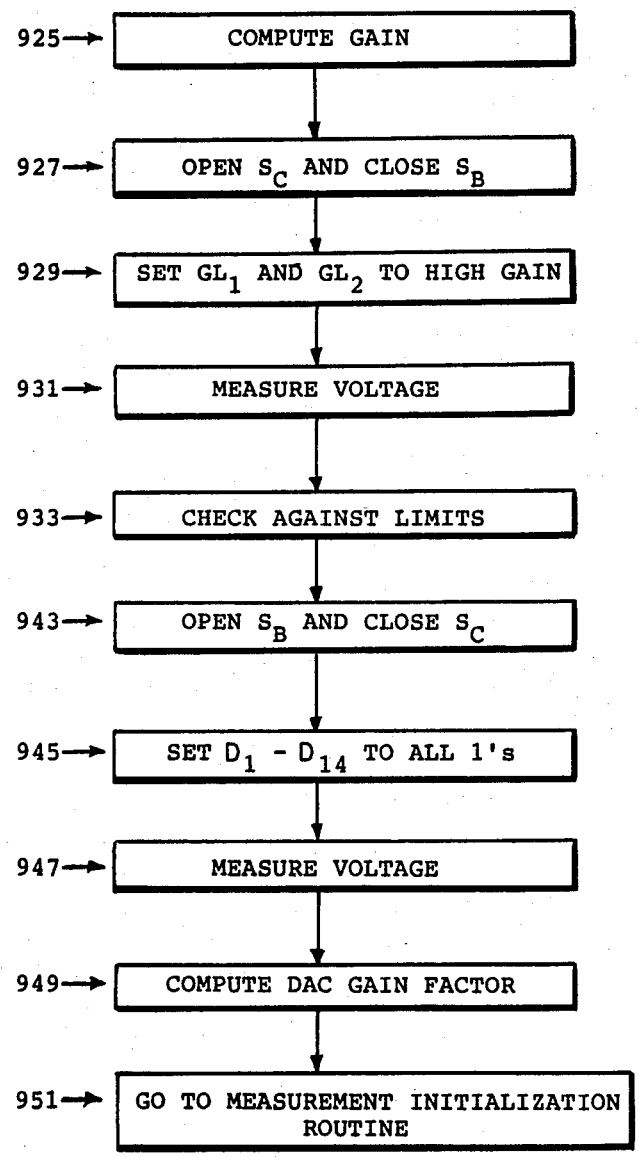

FIG. 9 shows the calibration routines. First, the zero offset error of DAC 296 is measured, blocks 901-915. To begin, multiplexer 330 is commanded to select the EM signal for measurement, block 901, and multiplexer 352 is commanded to select the 0-degree clock signal as the demodulating signal, block 903. Both gain control signals $GC_1$ and $GC_2$ are set to the high gain state, block 905. Switch $S_A$ is closed to provide a ground reference to one input of comparator 292, block 907. Next, the digital inputs $D_1-D_{14}$ to DAC 296 are all set to zero, block 909. The differential input voltage to comparator 292 at this point is the difference between ground and the zero output voltage from DAC 296. This voltage is measured, block 911, and the zero offset error from DAC 296 is computed, block 913. This value is checked against its limit values, block 915. If the error is within acceptable limits, the offset error value is stored and used to correct later measurements.

Next, the A/D converter is calibrated to determine the output from the A/D converter which is equivalent to one turn of the secondary windings on transformer 236. With the gain still at high and the DAC output still at 0, switch $S_A$ is opened and switch $S_C$ is closed to connect the output from the two turn winding 286 to the measurement circuitry, block 921. The voltage is measured, block 923, and the gain from the input of comparator 292 through the A/D output is computed, block 925.

Next, the gain reduction factors controlled by $GC_1$ and $GC_2$ are computed. First, switch $S_C$ is opened and Switch $S_B$ is closed, block 927. The input to the comparator is now precisely 32 times larger, due to the precision of the outputs from transformer 236. The processor then sets the $GC_1$ and $GC_2$ signals to select high gain, block 929. The voltage is measured, block 931, and the ratio between the two gain settings is computed and stored, block 935.

The gain of DAC 296 and resistive divider 298-299 is then calibrated. Switch $S_B$ is opened and switch $S_C$ is closed to connect the 2-turn winding 286 to the comparator, block 943. The processor sets the $D_1-D_{14}$ inputs to DAC 296 all high, block 945. The voltage is then measured, block 947. By comparing this voltage with the voltage measured in block 923, the gain factor of the DAC and the 64:1 resistive divider can be coputed, block 949. This completes the calibration routine. The various correction factors determined during the calibration are used to determine the actual voltages from the measured voltages in the measurement routines described below.

Figure 10A:
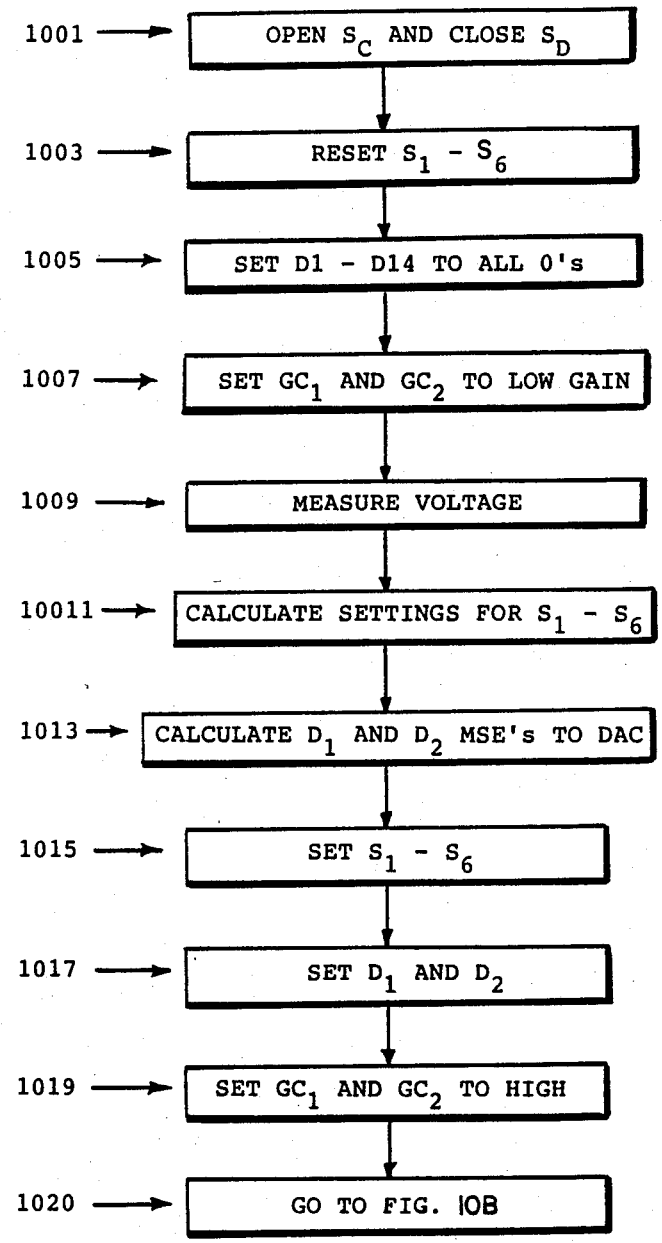
Figure 10C:
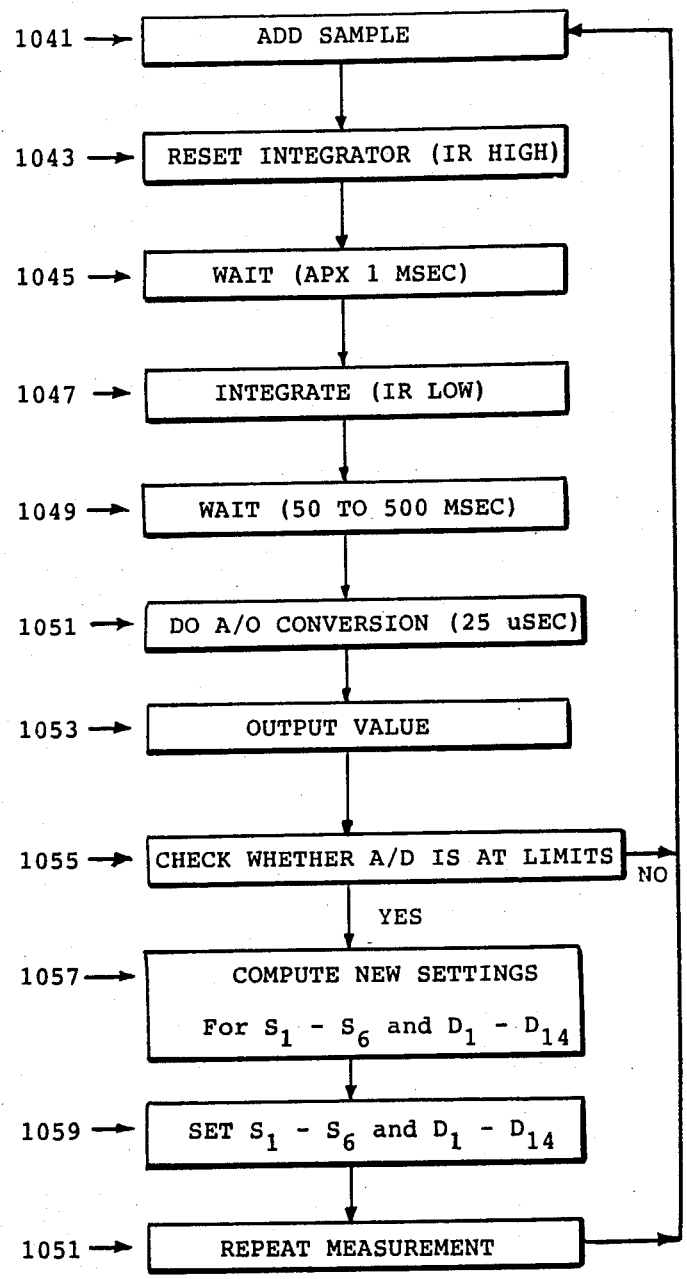
Figure 10B:
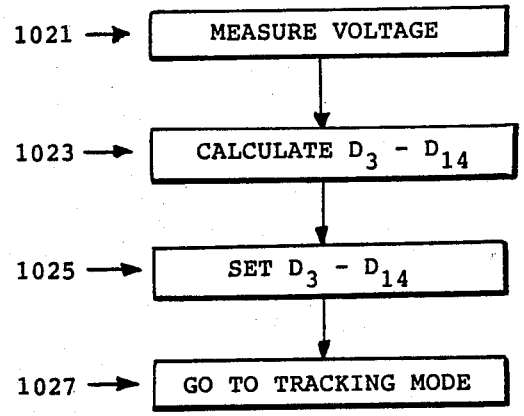

FIGS. 10A and 10B show the routine by which the conductivity change is measured. First, an initial routine, shown in FIG. 10B, is performed to quickly set switches $S_1-S_6$ and the DAC to their initial values. To do this, switch $S_C$ is opened and switch $S_D$ is closed to measure the voltage from the series connection of windings 270, 272, and 274-184, block 1001. The $D_1-D_{14}$ inputs to the DAC are set to 0, block 1003, and switches $S_1-S_6$ are set to deselect all six of the selectable windings of transformer 236, block 1007.

At this point the signal applied to the measurement circuitry is the difference between the test and control cell voltages. This voltage will typically be a fairly large value due to the difference between the bioregions with and without the receptors in the matrix, or due to other differences between the symmetry of the two fluid channels. Because of this the gain is set to the low value, block 1007, to prevent saturation of the measurement circuitry. The voltage is then measured, block 1009. From this measurement, as corrected by the factors determined during claibration, the processor computes the proper settings for switches $S_1$–$S_6$ and the two MSB's of DAC 296, blocks 1011 and 1013.

$S_1$–$S_6$ and the MSB's $D_1$ and $D_2$ are set by the processor, blocks 1015 and 1017. The gain is set to high, block 1019, and the voltage is again measured, block 1021. The processor then computes the value of the 12 LSB's of the DAC, block 1023, and the processor sets DAC lines $D_3$–$D_{14}$ to these values, block 1025. At this point, the difference between the voltages to comparator 292 should be less than one LSB of the DAC output. The processor then goes to the tracking routine shown in FIG. 10B.

At the beginning of the tracking routine, the sample to be analyzed is added to the electrolyte, block 1041. This may be done under control of the processor or manually in response to a prompt from the processor. Next, the integrator is reset. First, the processor sets the IR signal high to reset the integrator, block 1045. The processor waits for a short period of approximately 1 millisecond to allow the integrator capacitor to fully discharge, block 1045. The processor then sets the IR signal low, block 1947, to begin the integration of the voltage being measured.

The integrator is allowed to integrate for a selected period of time, block 1049, typically 50 to 500 milliseconds. At the end of the integration period, the processor commands the D/A converter to do a conversion, block 1051. The conversion takes approximately 25 microseconds, which is essentially instantaneously in terms of the rate of change of the integrator output signal. The A/D digital output is stored for later processing, block 1053.

Next, the processor checks to see whether the A/D converter is approaching the limits of its dynamic range, block 1055. If not, the processor returns to block 1043, and the above process is repeated. If the A/D is approaching the limits of its measurement range, the processor computes new settings for switches $S_1$–$S_6$ and/or DAC inputs $D_1$–$D_{14}$ which will return the voltage measured by the A/D converter to the center of its measurement range, block 1057, and these values are sent to the switches and DAC, block 1061. The processor then returns to block 1043 and the above process is repeated.

Figure 11:
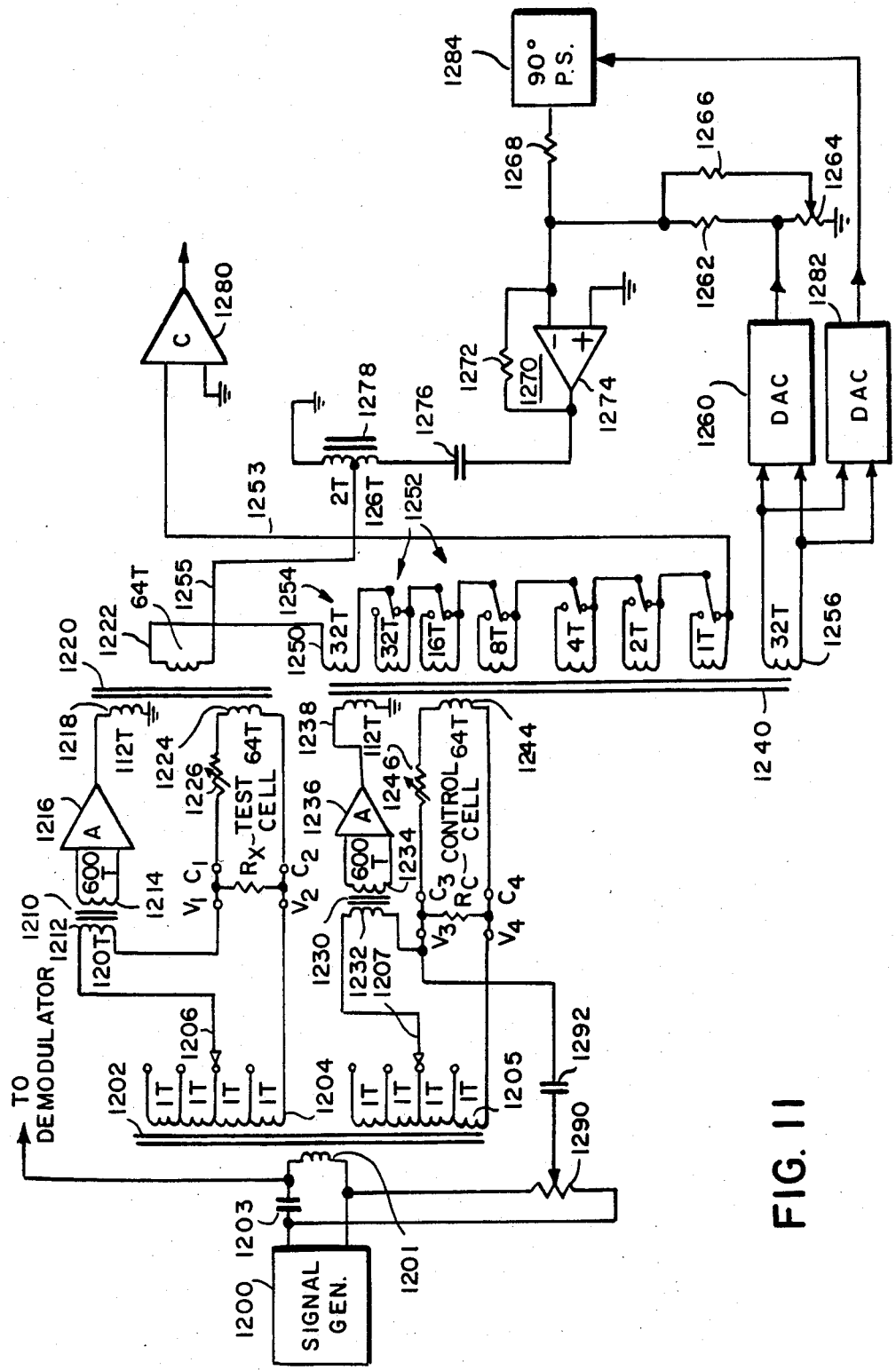
FIG. 11 shows an alternate embodiment for the embodiment shown in FIG. 2 for use with test and control cells using four-terminal measurements.

FIG. 11 shows an alternate embodiment of the ciruitry shown in FIG. 2 for the present invention. This circuitry was used in making the measurements used in most of the examples set forth in the above-referenced patent application by D. Mitchell and R. Mitchell. The circuitry of FIG. 11 is similar in many respects to the circuitry described previously, and the explanation below will point out the differences between the circuitry of FIG. 11 and the circuitry already discussed.

The circuitry of FIG. 11 is designed to work with a test and control cell structure which provides individual current electrode pairs for the test cell fluid path and the control cell fluid path, so that four-terminal measurements are made for both the test and control cells. These electrodes are shown schematically by electrodes 1298 and 1299 in FIG. 1A. Further details of four-terminal cell designs are set forth in the referenced application of D. Mitchell and R. Mitchell.

In FIG. 11, a signal generator 1200 applies a sine wave signal to an input winding 1201 of a transformer 1202 via a capacitor 1203. In this embodiment, the frequency of signal generator 1200 is 3 kHz. Transformer 1202 has two, identical, output windings 1204 and 1205. Winding 1204 has four output taps, and the output is taken from one of these taps via a 4-pole switch 1206. The primary winding of transformer 1202 has 140 turns on a supermalloy toroidial core, and each of the taps on secondary windings 1204 and 1205 are single turn windings. The two secondary windings provide individual current sources for the test and control cells.

The output from one of the taps on winding 1204, as selected by switch 1206, is applied to one end of the input winding 1212 of a transformer 1210. The other end of winding 1212 is connected to the first voltage measurement terminal $V_1$ of the test cell. The test and control cell resistances are denoted by $R_x$ and $R_c$ respectively. The second voltage terminal $V_2$ of the test cell is connected to the common end of winding 1204.

Transformer 1210 has a 600-turn secondary winding 1214 which drives a high-gain, tuned, AC amplifier 1216. Amplifier 1216 is similar to the AC amplifier shown in FIG. 6, but modified to work at the 3 kHz center frequency. The output of amplifier 1216 drives a 112-turn input winding 1218 to transformer 1220. Transformer 1220 is a precision ratio transformer. A 64-turn feedback winding 1214 is connected in series with a variable resistor 1226 to the two current electrodes $C_1$ and $C_2$. A 64-turn output winding on transformer 1220 provides an output signal.

Transformers 1210 and 1220 and amplifier 1220 are connected to provide a negative feedback loop. Due to the high gain of amplifier 1216 and the negative feedback provided through the transformers, the input to amplifier 1216 can be considered to be a virtual short circuit, and the voltage drop across winding 1212 is essentially zero. Thus the voltage across terminals $V_1$ and $V_2$ is nearly equal to the voltage from transformer winding 1204. The feedback winding 1224 drives a current through resistor 1226 and the test cell resistance $R_x$ to maintain the voltage drop across the voltage terminals $V_1$ and $V_2$ equal to the drive voltage from winding 1204. The current through and the voltage across the test cell is determined by the setting of switch 1206 and value of variable resistor 1226. The value of resistor 1226 is much greater than the test cell impedance to maintain a relatively contant impedance level as the test cell impedance changes. Resistor 1226 is typically on the order of 20-50 kilohms. Resistors 1226 and 1246 are adjusted to obtain a desired signal level from the amplifiers so that the following circuitry does not saturate and to match the amplitudes of the outputs from the test and control cells.

The control cell voltage terminals $V_3$ and $V_4$ and current terminals $C_3$ and $C_4$ are driven by and connected to circuitry identical to the circuitry described above in connection with the test cell, including tapped transformer winding 1205, transformers 1230 and 1240, and amplifier 1236.

Transformers 1220 and 1240 are analagous to transformers 216 and 236 shown and described above in reference to FIG. 2. Transformer 1220 has a single 64-turn output winding 1222 which provides a signal representative of the voltage drop across the test cell impedance. Transformer 1240 has a 32-turn winding 1250 and six, binary-weighed windings 1252 having 32, 16, 8, 4, 2, and 1 turns respectively. Six switches 1254 selectively connect windings 1252 in series with a the 64-turn output winding from transformer 1220 and a fixed 32-turn winding 1250 on transformer 1240. These windings allow the control cell output to be scaled over a range of about 0.5 to 1.5 times the test cell output, depending on the setting of switches 1252, with a precision of six bits.

The series connection and phasing of these windings effectively subtracts the control cell output signal, as scaled by the settings of switches 1254, from the test cell output signal. This difference signal is across lines 1253 and 1257 and is applied to comparator circuitry 1280 via an auto-transformer 1278, as explained below. The operation of the circuitry in comparator 1280 is similar to the compartor circuitry shown and described in FIG. 3.

Switches 1254 provide six bits of scaling range. Fourteen additional bits of scaling are provided by a 14-bit multiplying DAC 1260 in a manner similar to that of FIG. 2. DAC 1260 may be implemented by a ICL 7134U unipolar D/A integrated circuit. The output from an independent 32-turn winding 1256 is applied to the input of the DAC 1260. DAC 1260 is controlled by the digital processor, similarly to DAC 296 in FIG. 2. The output from DAC 1260 is applied via a resistive network including resistors 1262-1268 and a capacitor 1276 to a unity-gain buffer amplifier 1270.

The output from buffer 1270 is applied to one end of the auto-transformer 1278. The other end of auto-transformer 1278 is grounded. The turns ratio of the two sections of the auto-transformer is 128 to 2. This scales the output of the DAC 1260 by a factor of 64 so that one MSB from the DAC is equivalent to the output from a one-half turn winding on transformer 1240. A 10K potentiometer 1269 in conjunction with 250K resistor 1260 and a 10.2K resistor 1262 all the output from the DAC to be trimmed so that it is exactly equal to one-half turn. Thus switches 1254 and DAC 1260 provide a 20-bit range over which the control cell output can be scaled to track the test cell output.

A second DAC 1282 is also driven by winding 1256. DAC 1282 may be implemented by a ICL 7134B bipolar D/A converter integrated circuit. The output from DAC 1282 is applied via a 90° phase shifter circuit 1284 and a 10K resistor 1268 to buffer amplifier 1270. Thus, the total input to amplifier 1270 is composed of in-phase and quadrature components. During the diagnostic and calibration phases, the digital processor measures the quadrature component in the output from the test cell and sets the digital input to DAC 1282 so that the quadrature component is cancelled or reduced to prevent saturation of the following measurement circuitry.

Further quadrature compensation may be optionally added by means of a potentiometer 1290 connected across the output terminals of signal generator 1200 and a capacitor 1292 connecting the wiper of pot 1290 to terminal $V_3$. Typical values for these components are 5 kilohms and 100 pf. The setting of potentiometer 1290 may be adjusted to compensate for small amounts of quadrature error caused by capacitive loading.

The procedures followed in measuring conductivity using the alternate embodiment shown in FIG. 11 are similar to those described above and illustrated in FIGS. 8A–10C. A source code listing of a program for implementing these procedures with the embodiment of FIG. 11 is attached hereto as Appendix A. This listing is written in Basic and is for controlling a Hewlet Packard Computer Model 9845 to perform the described measurements.

There has been described a new method and apparatus for measuring the relative change in conductivity of test and control cells as described herein for determining the presence and/or concentration of an analyte in an electrolyte solution. The apparatus described herein is designed to be flexible enough to be able to perform a large variety of different measurements in different situations under control of a digital processor. It should be appreciated that specialized instruments designed for making measurements of specific types may not require or contain all of the features contained in the preferred embodiments disclosed herein and that the teachings herein may be modified, abridged, or adapted by those of ordinary skill in the art in implementing the present invention in different situations. Accordingly, the description of exemplary preferred embodiments should not be taken as a limitation on the scope of present invention, and the invention should be interpreted in accordance with the following claims.

APPENDIX A

```
10  !******** ( 18 OCT 1984 "BS_COR" ( GPIB @ PLOTTING) **************
20  !
30  !
40    COM Time,A$,T,Bits,Answer$,Stabilise_time,Routine,Ans$,Plot$,Print$,Gain,Bit
s$,I,Av$,Samples,Scale,Scans,Gra$,Hardcopy$,Gain_,Interval,Cycle,B$
50    COM Date_$,Run,Title$,Add_desc1$,Add_desc2$,Biolayer$,Sensor_desc$,U$[25]
60    COM Ratio1,Slope
70    COM SHORT Out2(10000)
80    ON KEY #0 GOSUB Pri
90    ON KEY #1 GOSUB Gra
100   ON KEY #15 GOTO Dump
110   ON KEY #3 GOTO 5900
120   RESET 7
130   PRINTER IS 16
140   Replot$="N"
150   GCLEAR
160   EXIT GRAPHICS
170   IF Cycle=0 THEN GOTO 220
180   PRINT PAGE
190   PRINT "DO YOU WISH TO REPLOT PREVIOUS DATA TO A DIFFERENT SCALE...(Y/N)"
200   INPUT Replot$
210   IF Replot$="Y" THEN GOSUB Replot
```

```
220 PRINT PAGE
230 U$=".....PREVIOUSLY WAS....."
240 PRINT "ENTER SENSOR DESCRIPTION";U$;Sensor_desc$
250 INPUT Sensor_desc$
260 PRINT PAGE
270 PRINT "ENTER BIOLAYER DESCRIPTION";U$;Biolayer$
280 INPUT Biolayer$
290 PRINT PAGE
300 PRINT "ENTER ANY ADDITIONAL DESCRIPTION";U$;Add_desc1$
310 INPUT Add_desc1$
320 PRINT PAGE
330 PRINT "ENTER DATE",Date_$
340 INPUT Date_$
350 PRINT PAGE
360 PRINT "ENTER RUN NUMBER.....PREVIOUS RUN WAS ";Run
370 Run=Run+1
380 PRINT "NEW RUN WILL BE ";Run;" UNLESS ANOTHER IS ENTERED"
390 INPUT Run
400 PRINT PAGE
410 PRINT "ENTER TITLE.....PREVIOUS TITLE WAS.... ";Title$
420 INPUT Title$
430 PRINT PAGE
440 PRINT "DO YOU WISH TO CHANGE ANY KEYBOARD INPUTS.....(Y or N)"
450 INPUT Answer$
460 PRINT PAGE
470 PRINT "DO YOU WANT HARD COPY....(Y/N)"
480 INPUT Hardcopy$
490 PRINT PAGE
500 IF Answer$="N" THEN GOTO Executive
510 PRINT "PRESENT GAIN LEVEL IS ";Gain_;" DO YOU WISH TO CHANGE IT"
520 PRINT "IF NOT PRESS CONT KEY"
530 PRINT "OTHERWISE ENTER DESIRED GAIN LEVEL"
540 PRINT
550 PRINT "ENTER DESIRED GAIN LEVEL"
560 PRINT "Normal gain level is 3 for a stable sensor or where the variations"
570 PRINT "are small.For a situation where the output is varying rapidly"
580 PRINT "use lower gain levels (2 for moderate situations 1 or 0 for"
590 PRINT "more extreme situations"
600 INPUT Gain_
610 PRINT PAGE
620 ! PRINT "ENTER SAMPLING INTERVAL...(Seconds)"
630 ! RINT "Recommended interval is 0.5 Seconds....(DO NOT EXCEED 2 sec)"
640 ! RINT "If you do not want to change it press CONT key."
650 ! INPUT Interval
660 Interval=.5
670 Time=20000*Interval
680 Stabilise_time=10
690 Bits=20
700 PRINT PAGE
710 PRINT "DO YOU WANT ANY DATA AVERAGING.....(Y/N)"
720 INPUT Av$
730 PRINT PAGE
740 IF Av$="N" THEN Samples=1
750 IF Av$="N" THEN GOTO 800
760 PRINT "PRESENT NUMBER OF SAMPLES IS ";Samples;" DO YOU WISH TO CHANGE IT "
770 PRINT "ENTER NUMBER OF SCANS PER AVERAGE"
780 INPUT Samples
790 PRINT PAGE
800 PRINT "SELECT PAIR  A & B OR PAIR C & D...(A=A&B    C=C&D)"
810 INPUT B$
820 IF B$="A" THEN A$="A"
830 IF B$="C" THEN A$="B"
840 GOSUB Unstick
850 OUTPUT 720;"C";A$
860 PRINT PAGE
870 PRINT "DO YOU WANT A GRAPHICAL OUTPUT"
880 INPUT Gra$
890 IF Gra$="Y" THEN GOSUB Plot_data
900 GOTO Executive
910 !
920 !
930 Plot_data:!
940 PRINT PAGE
```

A-1

```
950  PRINT "WHAT FULL SCALE SENSITIVITY ON THE GRAPH DO YOU WANT..(ppm)"
960  INPUT Scale
970  PRINT PAGE
980  PRINT "HOW MANY SCANS FULL SCALE DO YOU WANT ON THE TIME AXIS"
990  INPUT Scans
1000 RETURN
1010 !
1020 !
1030 Unstick:!
1040 SET TIMEOUT 7;T/3
1050 ON INT #7 GOSUB Bomb
1060 RETURN
1070 !
1080 !
1090 Init_quad:!
1100 GOSUB Unstick
1110 OUTPUT 720;"R0"
1120 OUTPUT 720;"L";32;",";0
1130 Quad1=Quad2=Qbit=0
1140 RETURN
1150 !
1160 !
1170 Init_ref:!
1180 GOSUB Unstick
1190 OUTPUT 720;"R9"
1200 OUTPUT 720;"L0,0"
1210 OUTPUT 720;"M0"
1220 Data1=Data2=Data3=Bit=0
1230 RETURN
1240 !
1250 !
1260 Set_hi_ref:!
1270 GOSUB Unstick
1280 M=6-Bit
1290 Data1=Data1+2^M
1300 OUTPUT 720;"M";Data1
1310 RETURN
1320 !
1330 !
1340 Set_hi_quad:!
1350 GOSUB Unstick
1360 M=6-Qbit
1370 Quad1=Quad1+2^M
1380 OUTPUT 720;"L";Quad1;",0"
1390 RETURN
1400 !
1410 !
1420 Set_mid_ref:!
1430 GOSUB Unstick
1440 M=12-Bit
1450 Data2=Data2+2^M
1460 OUTPUT 720;"L";Data2;",0"
1470 RETURN
1480 !
1490 !
1500 Set_lo_quad:!
1510 GOSUB Unstick
1520 M=14-Qbit
1530 Quad2=Quad2+2^M
1540 OUTPUT 720;"L";Quad1;",";Quad2
1550 RETURN
1560 !
1570 !
1580 Set_lo_ref:!
1590 GOSUB Unstick
1600 M=20-Bit
1610 Data3=Data3+2^M
1620 OUTPUT 720;"L";Data2;",";Data3
1630 RETURN
1640 !
1650 !
1660 A_to_d:!
1670 SET TIMEOUT 7;T/3
```

A-2

```
1680 ON INT #7 GOSUB Bomb
1690 OUTPUT 720;"S";T
1700 SET TIMEOUT 7;T
1710 WAIT T/3
1720 ENTER 720;Y;Z
1730 SYSTEM TIMEOUT OFF
1740 OFF INT #7
1750 Adc=Y-128
1760 RETURN
1770 !
1780 !
1790 Bomb:!
1800 BEEP
1810 SYSTEM TIMEOUT OFF
1820 OFF INT #7
1830 ABORTIO 7
1840 RESET 7
1850 Gerr=Gerr+1
1860 RETURN
1870 !
1880 !
1890 Gain1:!
1900 OUTPUT 720;"G1"
1910 Gain=1
1920 RETURN
1930 !
1940 !
1950 Gain2:!
1960 OUTPUT 720;"G2"
1970 Gain=2
1980 RETURN
1990 !
2000 !
2010 Gain3:!
2020 OUTPUT 720;"G3"
2030 Gain=3
2040 RETURN
2050 !
2060 !
2070 Gain0:!
2080 OUTPUT 720;"G0"
2090 Gain=0
2100 RETURN
2110 !
2120 !
2130 Executive:!
2140 IF Gra$="Y" THEN GOSUB Graph
2150 EXIT GRAPHICS
2160 PRINT PAGE
2170 Ratio2=Cycle=0
2180 PENUP
2190 T=Time/25
2200 DISP "SET GAIN TO LEVEL ";Gain_
2210 ON Gain_+1 GOSUB Gain0,Gain1,Gain2,Gain3
2220 ! WAIT 1000
2230 DISP "INITIALIZE QUADRATURE"
2240 GOSUB Init_quad
2250 ! WAIT 1000
2260 DISP "INITIALIZE REFERENCE"
2270 GOSUB Init_ref
2280 ! WAIT 1000
2290 DISP "DIGITIZE REFERENCE...(PRELIMINARY)"
2300  GOSUB Digitize_ref
2310 DISP "DIGITIZE QUADRATURE....(PRELIMINARY)"
2320 GOSUB Init_quad
2330  GOSUB Quadrature
2340  !
2350  !
2360 Is_quad_ok:!
2370 GOSUB Unstick!
2380 OUTPUT 720;"R0"!
2390 GOSUB A_to_d !                    THIS ROUTINE CHECKS TO SEE THAT
2400 IF ABS(Adc)<126 THEN GOTO 2490!   QUADRATURE HAS BEEN CORRECTLY
2410 PRINT PAGE !                      BALANCED.
```

A-3

```
2420 FOR Z=1 TO 10!
2430 BEEP!
2440 NEXT Z!
2450 DISP "QUADRATURE PROBLEM....QUADRATURE DOES NOT BALANCE"
2460 END
2470 !
2480 !
2490 GOSUB Unstick
2500 OUTPUT 720;"R9"
2510 DISP "INITIALIZE REFERENCE...(PRECALIBRATE)"
2520 ! WAIT 250
2530  GOSUB Init_ref
2540 DISP "DIGITIZE REFERENCE...(PRECALIBRATE)"
2550  GOSUB Digitize_ref
2560  GOSUB Calibrate
2570  DISP "INITIALIZE REFERENCE...(PRE-TRACK)"
2580  GOSUB Init_ref
2590  DISP "DIGITIZE REFERENCE....(PRE-TRACK)"
2600  GOSUB Digitize_ref
2610  IF Gra$="Y" THEN GRAPHICS
2620  Ratio1=(524288+Data1*16384+Data2*256+Data3)/2^20
2630  Delta=ABS(Ratio1-Ratio2)
2640  Ratio2=Ratio1
2650  G=16^(3-Gain)
2660  IF Delta>.0001*G THEN GOTO 2580
2670  Gerr=0
2680  T=Time/25
2690  K=30000*I/Slope/T/16^(Gain-1)
2700  PRINT PAGE
2710  GOSUB A_to_d
2720  Adc1=Adc
2730  Ratio=(524288+Data1*16384+Data2*256+Data3-Adc*K)/2^20
2740  IF ABS(Ratio-Ratio1)>.01 THEN GOSUB Init_quad
2750  IF ABS(Ratio-Ratio1)>.01 THEN GOSUB Quadrature
2760  IF ABS(Ratio-Ratio1)>.01 THEN Ratio1=Ratio
2770  GOSUB Unstick
2780  OUTPUT 720;"R9"
2790  IF Cycle=0 THEN Aver_ratio=Ratio
2800  IF Cycle=0 THEN Out1=Ratio
2810  Cycle=Cycle+1
2820  DISP Cycle
2830  Aver_ratio=(Samples-1)/Samples*Aver_ratio+Ratio/Samples
2840  Out=INT(10^7*Aver_ratio+.5)/10^7
2850  C=.1*Cycle-INT(.1*Cycle)
2860  IF C=0 THEN GOTO 2880
2870  GOTO 2910
2880  IMAGE "D1=",DD,"|D2=",DDD,"|D3=",DDD,"|Q1=",DD,"|Q2=",DDD,"|Adc=",SDDD,"|Ratio=",D.DDDDDD,"|Ave=",D.DDDDDD
2890  PRINT USING 2880;Data1,Data2,Data3,Quad1,Quad2,Adc,Ratio,Out
2900  GOSUB Check_quad
2910  Out2(Cycle)=INT((Out-Out1)/Out1*1E7)/10
2920  IF Cycle<10 THEN GOTO 2940
2930  IF Gra$="Y" THEN PLOT Cycle-10,Out2(Cycle)
2940  IF ABS(Adc)>126 THEN GOSUB Init_ref
2950  IF ABS(Adc)>126 THEN GOSUB Digitize_ref
2960  IF Adc>100 THEN GOTO 2990
2970  IF Adc<-100 THEN GOTO 3010
2980  GOTO 2710
2990  Incr=INT(960000/Time)
3000  GOTO 3020
3010  Incr=-INT(960000/Time)
3020  GOSUB Increment_digi
3030  GOTO 2710
3040  !
3050  !
3060 Digitize_ref: !
3070  Bit=Bit+1
3080  IF Bit<7 THEN GOTO 3120
3090  IF Bit<13 THEN GOTO 3140
3100  IF Bit>12 THEN Stage=3
3110  GOTO 3150
3120  Stage=1
3130  GOTO 3150
3140  Stage=2
```

A-4

```
3150 ON Stage GOSUB Set_hi_ref,Set_mid_ref,Set_lo_ref
3160 WAIT Stabilise_time
3170 GOSUB A_to_d
3180 IF Adc<0 THEN GOSUB Bit_off
3190 IF Bit=Bits THEN RETURN
3200 GOTO 3070
3210 !
3220 !
3230 Bit_off:!
3240 ON Stage GOTO Range1,Range2,Range3
3250 !
3260 !
3270 Range1:!
3280 M=6-Bit
3290 Data1=Data1-2^M
3300 OUTPUT 720;"M";Data1
3310 RETURN
3320 !
3330 !
3340 Range2:!
3350 M=12-Bit
3360 Data2=Data2-2^M
3370 OUTPUT 720;"L";Data2;",0"
3380 RETURN
3390 !
3400 !
3410 Range3:!
3420 M=20-Bit
3430 Data3=Data3-2^M
3440 OUTPUT 720;"L";Data2;",";Data3
3450 RETURN
3460 !
3470 !
3480 Quadrature:!
3490 Qbit=Qbit+1
3500 IF Qbit<7 THEN GOSUB Set_hi_quad
3510 IF Qbit>6 THEN GOSUB Set_lo_quad
3520 WAIT Stabilise_time
3530 GOSUB A_to_d
3540 IF Adc>0 THEN GOSUB Qbit_off
3550 IF Qbit>13 THEN RETURN
3560 GOTO 3490
3570 !
3580 !
3590 Qbit_off:!
3600 IF Qbit<7 THEN GOTO Qbit1
3610 IF Qbit>6 THEN GOTO Qbit2
3620 !
3630 !
3640 Qbit1:!
3650 M=6-Qbit
3660 Quad1=Quad1-2^M
3670 OUTPUT 720;"L";Quad1;",0"
3680 RETURN
3690 !
3700 !
3710 Qbit2:!
3720 M=14-Qbit
3730 Quad2=Quad2-2^M
3740 OUTPUT 720;"L";Quad1;",";Quad2
3750 RETURN
3760 !
3770 !
3780 !
3790 !
3800 Graph:!
3810 PLOTTER IS 13,"GRAPHICS"
3820 GRAPHICS
3830 DEG
3840 MOVE 49*RATIO,1
3850 CSIZE 4
3860 LABEL "SCANS"
3870 MOVE 2.5*RATIO,50
3880 CSIZE 4
```

A-5

```
3890 LDIR 90
3900 LABEL "PPM"
3910 A=RATIO*9.5
3920 B=RATIO*97
3930 LOCATE A,B,10,98
3940 SCALE 0,Scans,-Scale,Scale
3950 MOVE 0,0
3960 LINE TYPE 3
3970 DRAW Scans,0
3980 LINE TYPE 1
3990 AXES .2*Scans,.5*Scale,0,-Scale
4000 LDIR 0
4010 LORG 8
4020 CSIZE 3
4030 FOR Y=-Scale TO Scale STEP .5*Scale
4040 MOVE 0,Y
4050 IF Scale<100 THEN LABEL USING "MDD.DX";Y
4060 IF Scale>=100 THEN LABEL USING "MDDDDDDX";Y
4070 NEXT Y
4080 LDIR 0
4090 LORG 6
4100 FOR X=0 TO Scans STEP .2*Scans
4110 MOVE X,-Scale*1.05
4120 LABEL USING "DDDDD";X
4130 NEXT X
4140 RETURN
4150 !
4160 !
4170 !
4180 !
4190 Encode:!
4200 Data=Data1*16384+Data2*256+Data3+Incr
4210 RETURN
4220 !
4230 !
4240 Decode:!
4250 Data1=INT(Data/16384)
4260 Data2=INT((Data-Data1*16384)/256)
4270 Data3=Data-Data1*16384-Data2*256
4280 RETURN
4290 !
4300 !
4310 Set_d_to_a:!
4320 OUTPUT 720;"M";Data1
4330 OUTPUT 720;"L";Data2;",";Data3
4340 RETURN
4350 !
4360 !
4370 Calibrate:!
4380 PRINTER IS 16
4390 PRINT PAGE
4400 PRINT "CALIBRATION DATA"
4410 PRINT "*****************"
4420 PRINT
4430 Calibrate2:!
4440 GOSUB Gain1
4450 I=500
4460 T=I
4470 Acc_zero=0
4480 FOR N=1 TO 10
4490 GOSUB A_to_d
4500 Acc_zero=Acc_zero+Adc
4510 Zero(N)=Adc
4520 IF ABS(Zero(N)-Acc_zero/N)>5 THEN Error_flag=1
4530 NEXT N
4540 IF ABS(Acc_zero)>20 THEN GOTO Try_again
4550 PRINT "Mean Zero=";Acc_zero/10;"        !(Average of 10 samples)"
4560 Incr=30000
4570 GOSUB Encode
4580 GOSUB Decode
4590 GOSUB Set_d_to_a
4600 Acc=0
4610 FOR N=1 TO 10
```

```
4620 GOSUB A_to_d
4630 Acc=Acc+Adc
4640 Accum(N)=Adc
4650 IF ABS(Accum(N)-Acc/N)>5 THEN Error_flag=1
4660 NEXT N
4670 Slope=(Acc-Acc_zero)/10
4680 PRINT "Mean Accum=";Acc/10;"           (Average of 10 samples)"
4690 PRINT "Mean Slope Factor=";Slope;"     (Average of 10 samples)"
4700 WAIT 5000
4710 BEEP
4720 IF Error_flag=0 THEN GOTO 4860
4730 PRINT
4740 PRINT "DURING THIS CALIBRATION RUN ABNORMAL VARIATIONS IN VALUES "
4750 PRINT "WERE DETECTED.THE DATA ARE AS FOLLOWS"
4760 PRINT
4770 PRINT "SAMPLE","ZERO VALUE","FULLSCALE VALUE","SLOPE VALUE"
4780 FOR N=1 TO 10
4790 PRINT N,Zero(N),Accum(N),Accum(N)-Zero(N)
4800 NEXT N
4810 BEEP
4820 PRINT
4830 PRINT "OPERATION SUSPENDED....press CONT KEY if you wish to continue"
4840 PAUSE
4850 PRINT PAGE
4860 ON Gain_+1 GOSUB Gain0,Gain1,Gain2,Gain3
4870 IF Hardcopy$="N" THEN PRINTER IS 16
4880 Incr=-30000
4890 GOSUB Encode
4900 GOSUB Decode
4910 GOSUB Set_d_to_a
4920 BEEP
4930 IF Hardcopy$="N" THEN PRINTER IS 16
4940 RETURN
4950 !
4960 !
4970 Increment_digi:!
4980 GOSUB Encode
4990 GOSUB Decode
5000 GOSUB Set_d_to_a
5010 RETURN
5020 !
5030 !
5040 Pri:!
5050 EXIT GRAPHICS
5060 RETURN
5070 !
5080 !
5090 Gra:!
5100 GRAPHICS
5110 RETURN
5120 !
5130 !
5140 Dump:!
5150 PRINTER IS 16
5160 PRINT PAGE
5170 Add_desc2$=" "
5180 PRINT "ANY ADDITIONAL DESCRIPTION"
5190 INPUT Add_desc2$
5200 PRINTER IS 0
5210 PRINT PAGE
5220 PRINT TAB(25),Title$
5230 DUMP GRAPHICS
5240 PRINT "SENSOR DESCRIPTION:      ";Sensor_desc$
5250 PRINT "BIOLAYER:                ";Biolayer$
5260 PRINT "DATE:                    ";Date_$
5270 PRINT "RUN NUMBER:              ";Run
5280 PRINT "INITIAL RESISTANCE RATIO: ";INT(1E6*Ratio1+.5)/1E6
5290 PRINT "SAMPLES PER SCAN:        ";Samples
5300 PRINT "GAIN LEVEL               ";Gain_
5310 PRINT "MEAN SLOPE FACTOR:       ";Slope
5320 PRINT "COMMENTS:"
5330 PRINT Add_desc1$
5340 PRINT Add_desc2$
```

```
5350 PRINT
5360 GOTO 10
5370 !
5380 !
5390 Replot:!
5400 GOSUB Plot_data
5410 Base_line=100
5420 Out3=0
5430 PRINT "DO YOU WANT BASE LINE DRIFT CORRECTIONS....(Y=Yes   N=No)"
5440 INPUT Ans$
5450 IF Ans$="Y" THEN GOTO 5480
5460 Drift_per_scan=0
5470 GOTO 5660
5480 PRINT "ENTER No OF SCANS FOR START OF BASE-LINE DRIFT CORRECTION"
5490 PRINT "    (Default value=0 scans)"
5500 INPUT Begin
5510 PRINT
5520 PRINT
5530 PRINT "ENTER No OF SCANS FOR END OF BASE-LINE  DRIFT CORRECTION"
5540 PRINT "    ( Default value=100 scans)"
5550 INPUT End
5560 FOR N=Begin+1 TO .2*(End-Begin)+Begin
5570 Out3=Out3+Out2(N)
5580 NEXT N
5590 Out4=Out3*5/(End-Begin)
5600 Out3=0
5610 FOR N=Begin+1+.8*(End-Begin) TO End
5620 Out3=Out3+Out2(N)
5630 NEXT N
5640 Out5=Out3*5/(End-Begin)
5650 Drift_per_scan=(Out5-Out4)/.8/(End-Begin)
5660 IF Scans>Cycle THEN Scans=Cycle
5670 GOSUB Graph
5680 FOR N=1 TO Scans
5690 PLOT N,Out2(N)-Out2(Begin)-(N-Begin)*Drift_per_scan
5700 NEXT N
5710 GOTO 5710
5720 !
5730 !
5740 Check_quad:!
5750 GOSUB Unstick
5760 OUTPUT 720;"R0"
5770 GOSUB A_to_d
5780 IF ABS(Adc)<126 THEN GOTO 5810
5790 GOSUB Init_quad
5800 GOSUB Quadrature
5810 OUTPUT 720;"R9"
5820 RETURN
5830 !
5840 !
5850 Try_again:!
5860 DISP "RETRYING TO BALANCE QUADRATURE"
5870 FOR Z=1 TO 100
5880 BEEP
5890 NEXT Z
5900 GOSUB Init_quad
5910 GOSUB Quadrature
5920 GOSUB Init_ref
5930 GOSUB Digitize_ref
5940 GOTO Calibrate
5950 !
5960 !
5970 !
5980 !
5990 Sar:!
6000 DISP "INIT-QUAD"
6010 GOSUB Init_quad
6020 DISP "INIT-REF"
6030 GOSUB Init_ref
6040 Bits=20
6050 DISP "DIGITIZE REF"
6060 GOSUB Digitize_ref
6070 DISP "INIT QUAD    .....(LINE 6025)"
```

A-9

```
6080 GOSUB Init_quad
6090 DISP "QUADRATURE"
6100 GOSUB Quadrature
6110 DISP "INIT REF   (LINE 6035)"
6120 GOSUB Init_ref
6130 DISP "DIGITIZE REF  (LINE 6038)"
6140 GOSUB Digitize_ref
6150  Ratio=(524288+Data1*16384+Data2*256+Data3)/2^20
6160 PRINT "D1=";Data1,"D2=";Data2,"D3=";Data3,"Ratio=";INT(1E6*Ratio+.5)/1E6
6170 GOTO 6110
6180 !
6190 !
6200 Adj_msb_lsb:!
6210 INPUT "ENTER DESIRED GAIN",G
6220 ON G GOSUB Gain1,Gain2,Gain3
6230 GOSUB Init_ref
6240 GOSUB Digitize_ref
6250 GOSUB Init_quad
6260 GOSUB Quadrature
6270 GOSUB Init_ref
6280 GOSUB Low_data
6290 GOSUB Dig
6300 Adc_low=Adc
6310 GOSUB High_data
6320 GOSUB Dig
6330 Adc_high=Adc
6340 PRINT "LO=";Adc_low,"HI=";Adc_high
6350 GOTO 6280
6360 !
6370 !
6380 Low_data:!
6390 Data1=31
6400 Data2=63
6410 Data3=255
6420 RETURN
6430 !
6440 !
6450 High_data:!
6460 Data1=32
6470 Data2=0
6480 Data3=0
6490 RETURN
6500 !
6510 !
6520 Dig:!
6530 GOSUB Set_d_to_a
6540 GOSUB A_to_d
6550 RETURN
```

A-10

What is claimed is:

1. Apparatus for measuring the relative impedances of a test cell and a control cell, including:

signal generator means for causing AC current signals of a selected frequency to flow through the test cell and through the control cell so that the phase and magnitude of the current flowing through the test cell is substantially identical to the phase and magnitude of the current flowing through the control cell;

first amplifier means, responsive to the voltage drop across the test cell and including a first transformer having an output winding, for providing an output signal across the output winding proportional to the voltage drop across the test cell;

multiplier means reponsive to a first set of digital signals applied thereto for providing an output signal equal to a selected fractional part of the first transformer output signal;

second amplifier means, responsive to the voltage drop across the control cell and including a second transformer having a plurality of output windings, for providing output signals across each of the plurality windings proportional to the voltage drop across the control cell, the plurality of output windings having differing numbers of turns so that a signal proportional to the voltage drop across the test cell may be scaled over a range by connecting in series selected ones of the plurality of windings;

a plurality of switches responsive to a second set of digital signals applied thereto for selectively connecting in series individuals ones of the second transformer output windings to provide a combined output signal;

switching means for connecting the first transformer output signal in series with the combined output signal with opposite polarity;

means for measuring the the first transformer output signal to produce a first measurement signal;

means for measuring the signal across one or more output windings of the second transformer to produce a second measurement signal;

means responsive to the first and second measurement signals for applying signals to the plurality of switches so that selected ones of the plurality of output windings are connected in series so that the combined output signal approximates the first transformer output signal and for activating the switching means thereafter;

means for measuring the voltage resulting from the series-connected first and combined output signals and for providing a first set of digital signals to the multiplyer means so that its output signal approximates said resulting voltage; and means for measuring the difference between the multiplier means output signal and the series-connected first and combined output signals and for providing a signal representative thereof.

* * * * *

UNITED STATES PATENT AND TRADEMARK OFFICE
CERTIFICATE OF CORRECTION

PATENT NO. : 4,652,830
DATED     : March 24, 1987
INVENTOR(S) : Neil L. Brown

It is certified that error appears in the above-identified patent and that said Letters Patent is hereby corrected as shown below:

On the title page Item (22) should read
-- January 14, 1985 --.

Column 38, line 53 after "plurality" insert --of--.

Column 38, line 61, "individuals" should read
--individual--;

Column 40, line 4, "multiplyer" should read
--multiplier--.

Signed and Sealed this

Seventh Day of June, 1988

Attest:

DONALD J. QUIGG

*Attesting Officer*     Commissioner of Patents and Trademarks